(12) United States Patent
Westwick et al.

(10) Patent No.: US 7,488,583 B2
(45) Date of Patent: Feb. 10, 2009

(54) FRAGMENT COMPLEMENTATION ASSAYS FOR G-PROTEIN-COUPLED RECEPTORS AND THEIR SIGNALING PATHWAYS

(75) Inventors: John K. Westwick, San Ramon, CA (US); Brigitte Keon, Castro Valley, CA (US); Marnie L. MacDonald, Pleasanton, CA (US)

(73) Assignee: Odyssey Thera, Inc., San Ramon, CA (US)

( * ) Notice: Subject to any disclaimer, the term of this patent is extended or adjusted under 35 U.S.C. 154(b) by 115 days.

(21) Appl. No.: 10/947,368

(22) Filed: Sep. 23, 2004

(65) Prior Publication Data

US 2005/0181452 A1 Aug. 18, 2005

Related U.S. Application Data

(60) Provisional application No. 60/505,447, filed on Sep. 25, 2003.

(51) Int. Cl.
*G01N 33/566* (2006.01)
*C07K 14/705* (2006.01)
*C07K 19/00* (2006.01)
*C12N 15/62* (2006.01)

(52) U.S. Cl. .................. 435/7.1; 435/7.2; 435/7.21; 435/69.7; 436/501; 536/23.4

(58) Field of Classification Search .............. None
See application file for complete search history.

(56) References Cited

U.S. PATENT DOCUMENTS

| 5,891,646 A * | 4/1999 | Barak et al. .................. 435/7.2 |
| 6,294,330 B1 * | 9/2001 | Michnick et al. .............. 435/6 |
| 6,893,827 B1 * | 5/2005 | Palmer et al. ................ 435/7.1 |
| 7,166,424 B2 * | 1/2007 | Michnick et al. .............. 435/4 |

OTHER PUBLICATIONS

Remy et al. Clonal Selection in vivo Quantitation of Protein Interactions with Protein-Fragment Complementation Assays. May 1999, P.N.A.S. 96:5394-5399.*

* cited by examiner

*Primary Examiner*—John D Ulm
(74) *Attorney, Agent, or Firm*—Issac A. Angres

(57) ABSTRACT

The invention provides a method of screening a candidate drug, a compound library or a biological extract to identify activators or inhibitors of G-protein-coupled receptors or G-protein-coupled pathways, comprising: (A) using a fluorescent protein fragment complementation assay to construct an assay for one or more steps in a G-protein-coupled pathway; (B) testing the effects of the candidate drugs, compound library, or biological extract on the receptor or pathway of interest; and (C) using the results of the screening to identify specific agents that activate or inhibit the receptor or pathway of interest. The invention also provides a method for identifying a drug lead that modulates the activity of a G-protein-coupled pathway using a fluorescent protein fragment complementation assay. The method of the invention is used to identify agonists, antagonists, activators or inhibitors of G-protein coupled receptors or G-protein-coupled pathways.

8 Claims, 15 Drawing Sheets

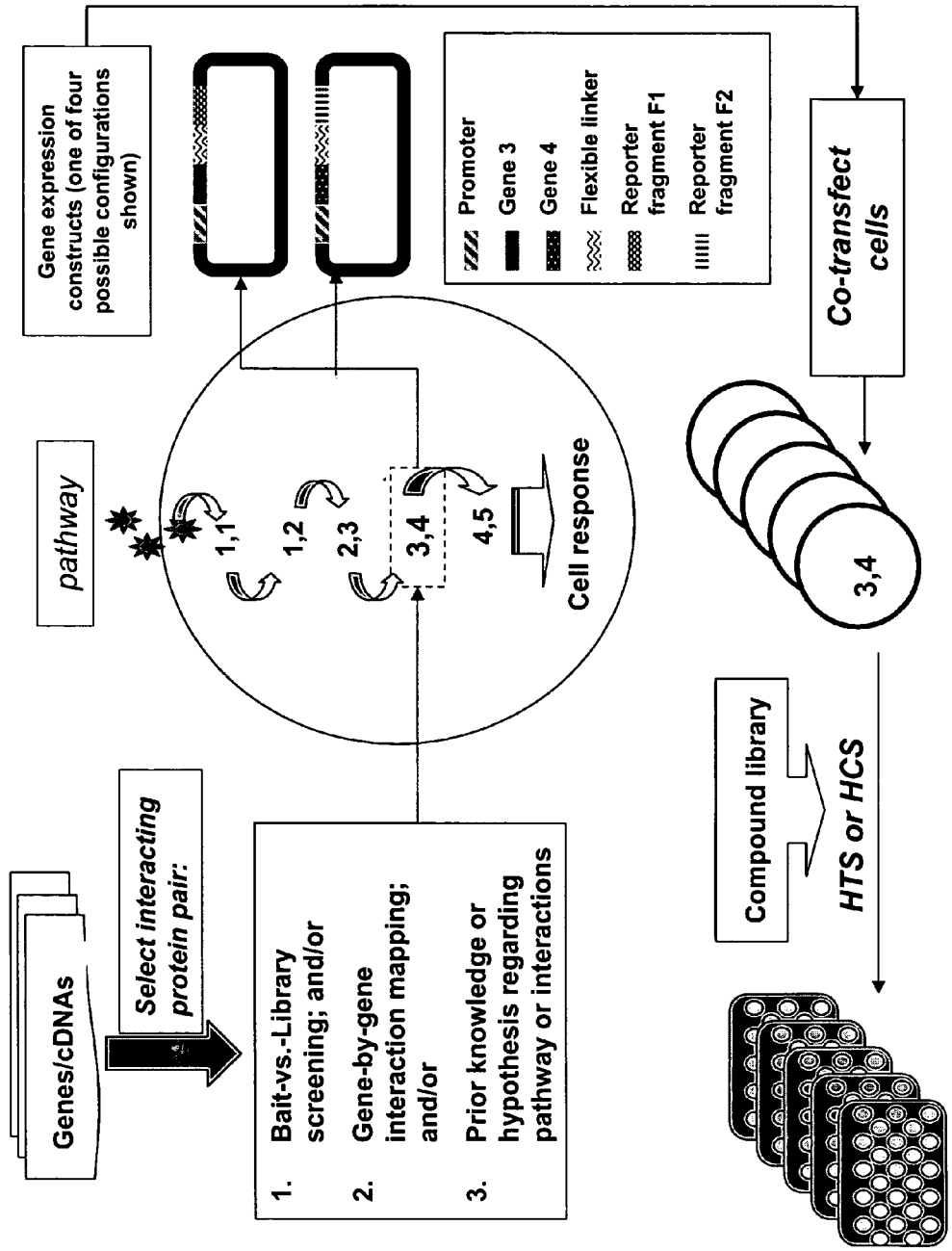
Fig. 1. General strategy for the design and construction of assays for G-protein-coupled receptors and G-protein-coupled pathways

Fig. 2 A protein-fragment complementation assay showing self-association of the β2-Adrenergic Receptor in living cells
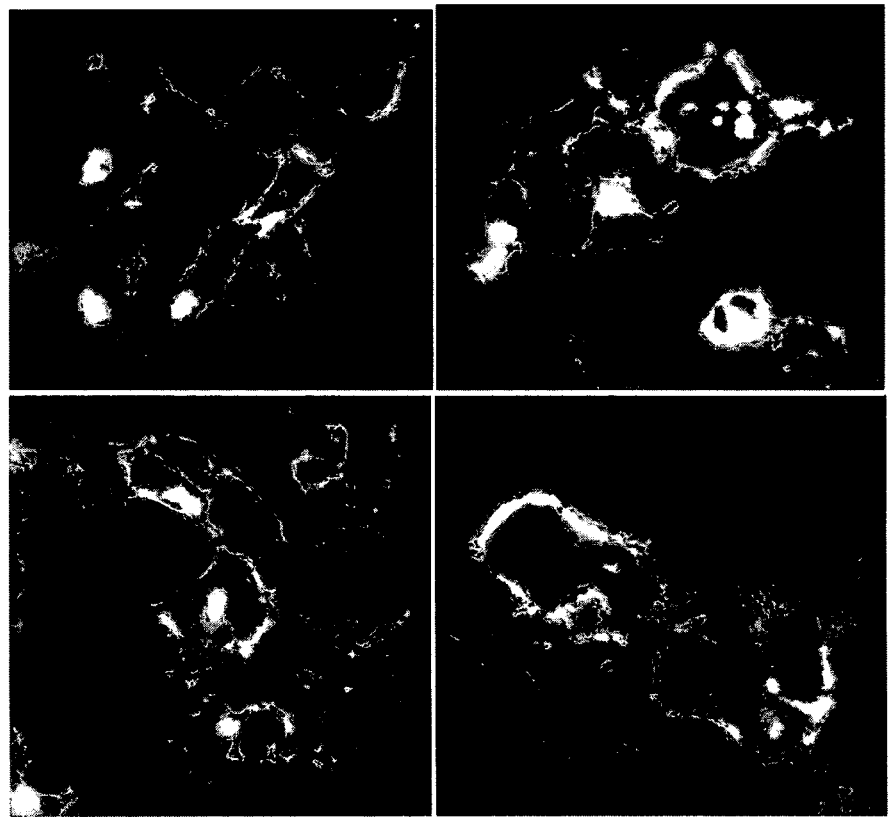

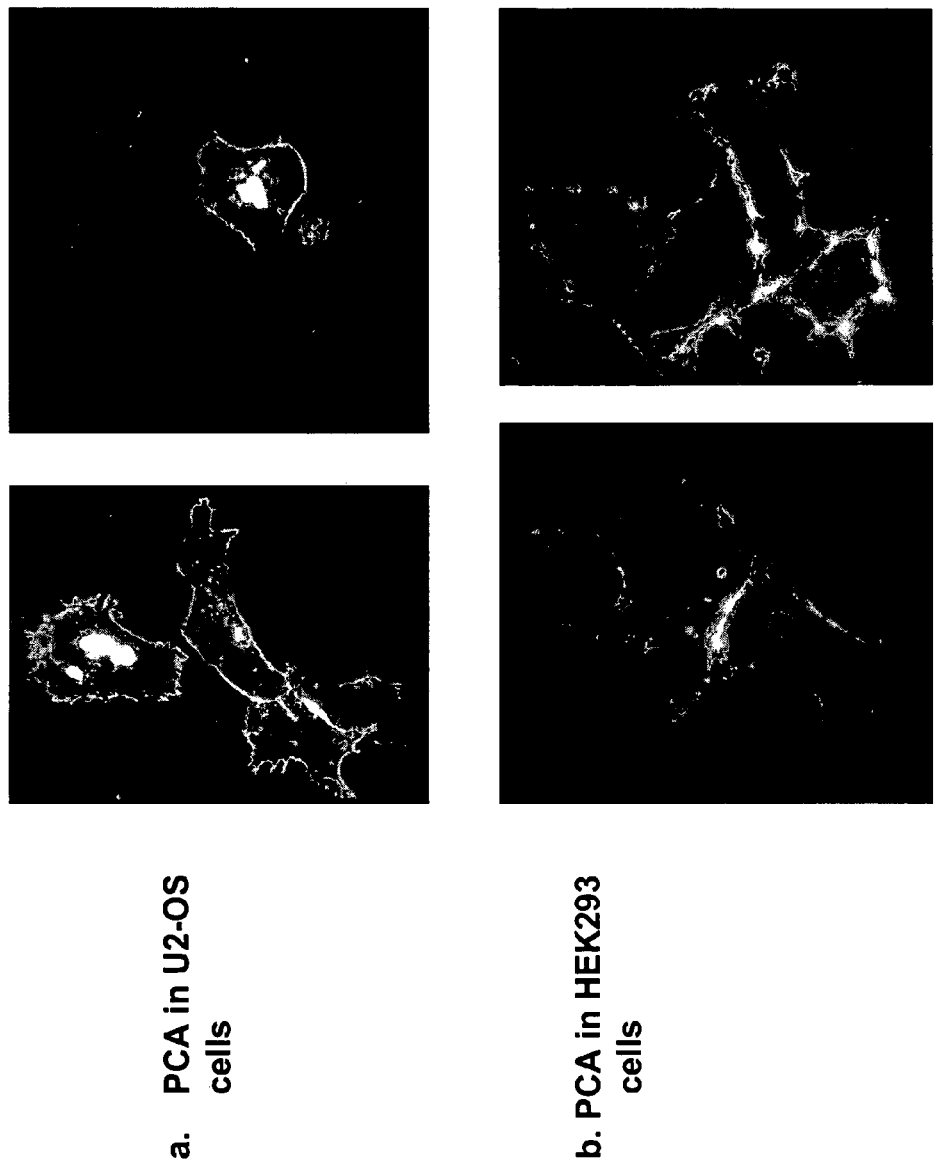
Fig. 3 A protein-fragment complementation assay showing association of the β₂Adrenergic Receptor with a G-protein α-subunit, Gαi, in two cell types
a. PCA in U2-OS cells
b. PCA in HEK293 cells

Fig. 4 A protein-fragment complementation assay showing association of the $\beta_2$-Adrenergic Receptor with the G-protein $\beta$-subunit, G$\beta$1, in HEK293E cells

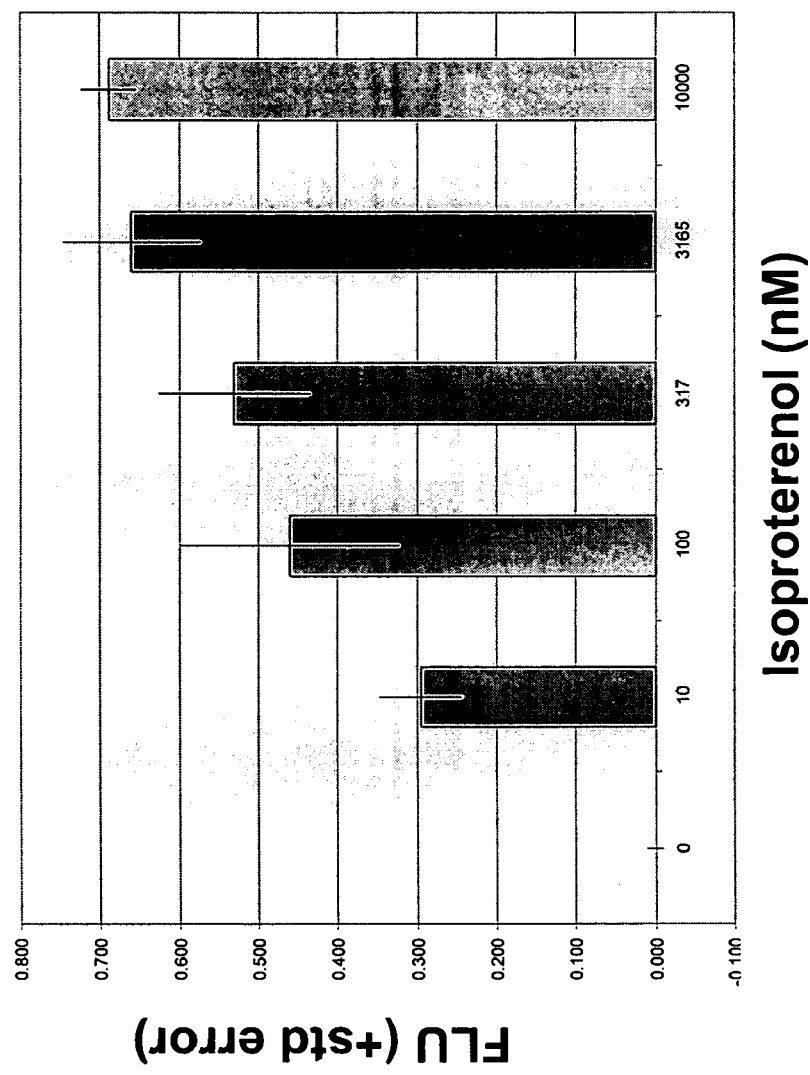
Fig. 5 A quantitative assay demonstrating agonist-dependent association of the $\beta_2$ Adrenergic Receptor with $\beta$-arrestin2

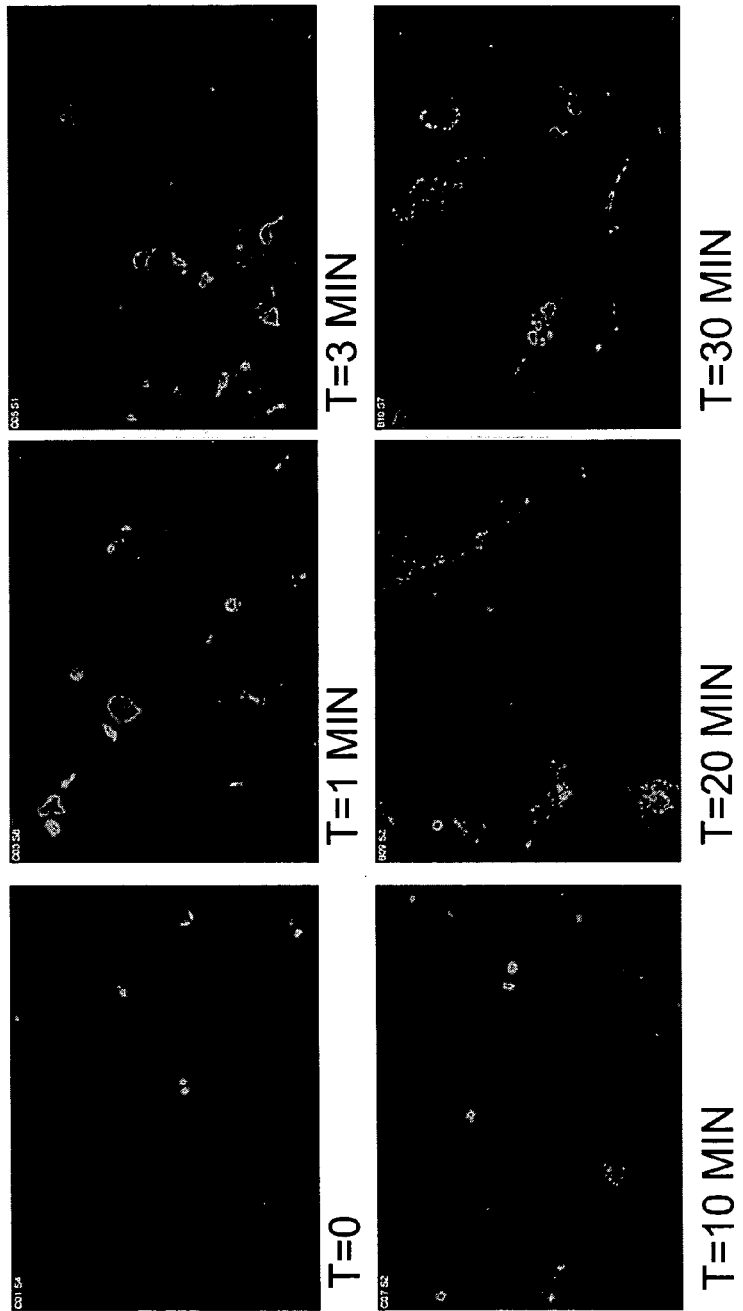
Fig. 6 A high-content, kinetic assay for the association of beta-arrestin with a GPCR showing the time course of response to agonist

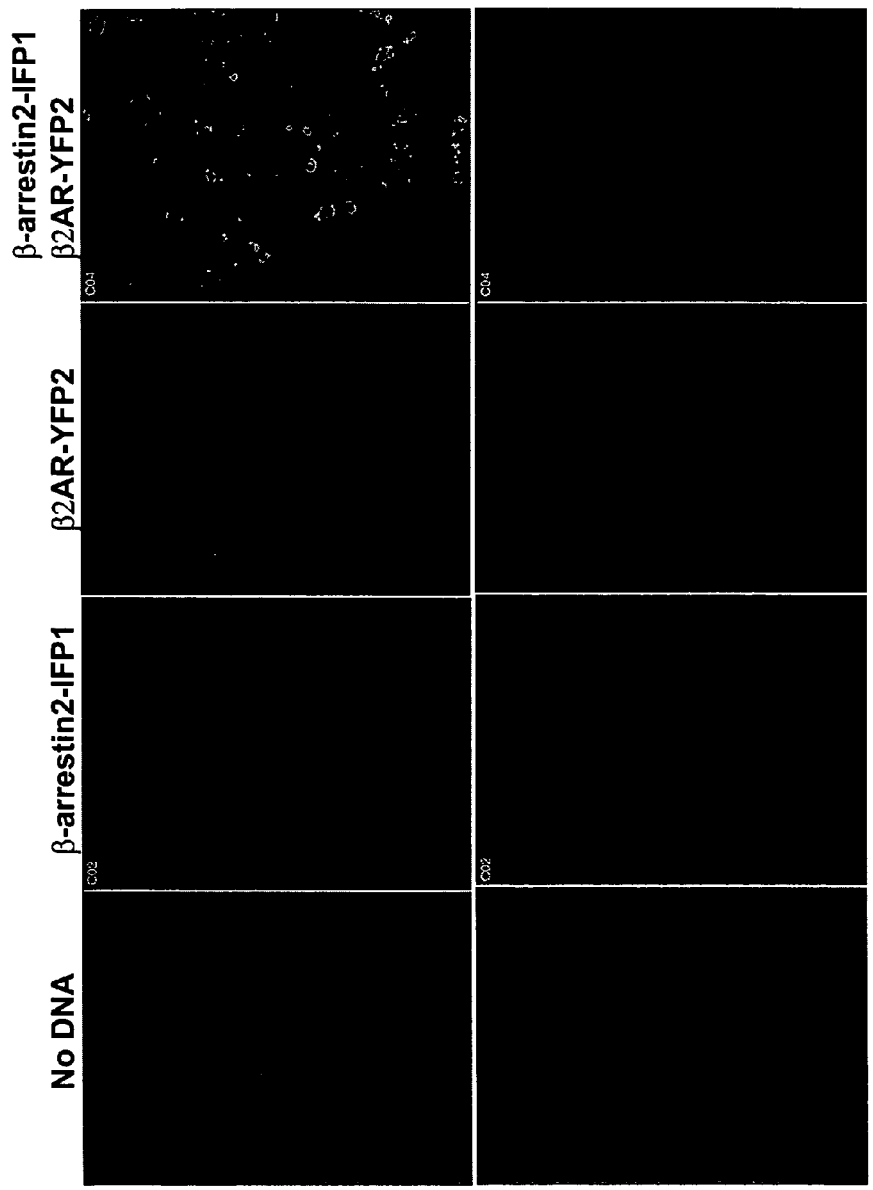
Fig. 7 Demonstration that PCA reporter fragments are not optically detectable molecules. The signal is generated only upon assisted complementation of two fragments that are separately fused to interacting molecules.

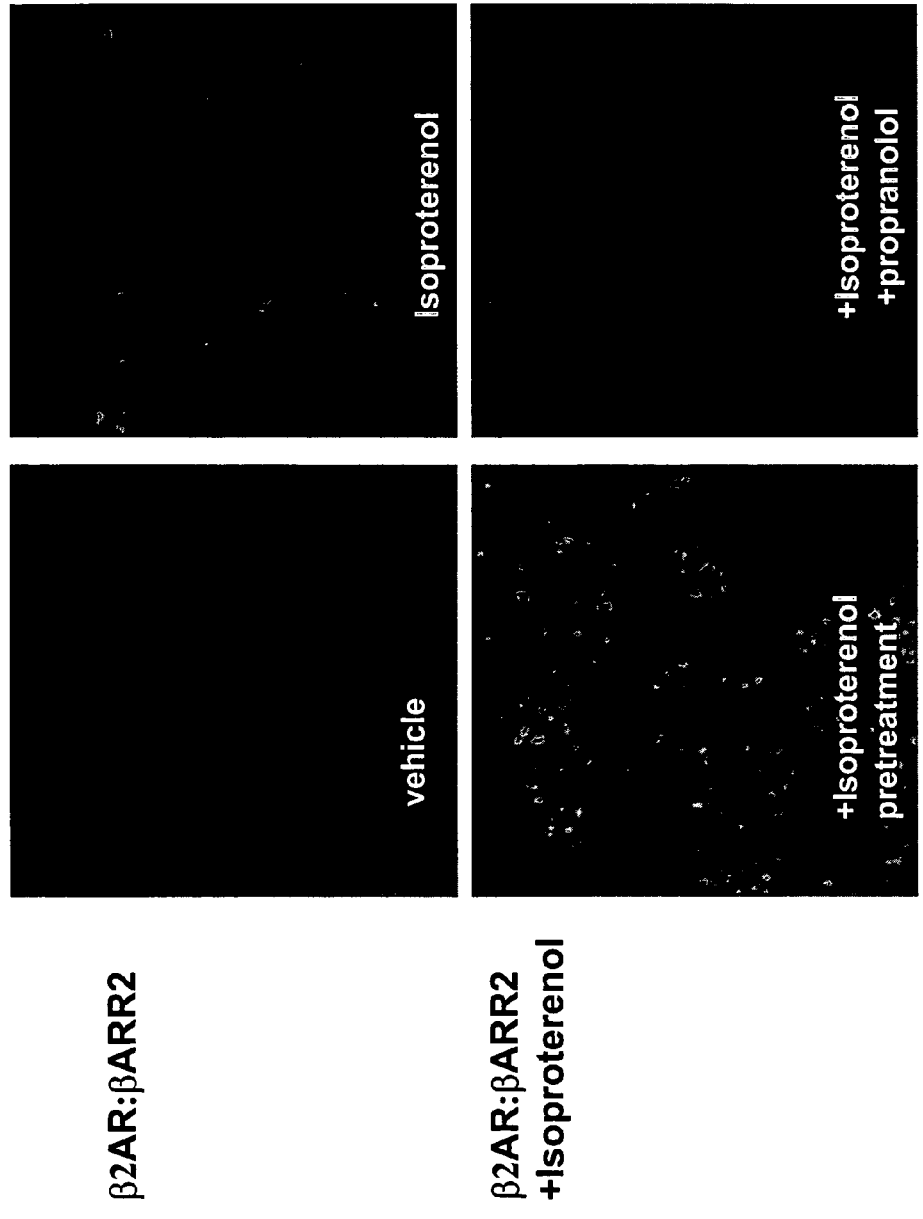
Fig. 8 Demonstration of the effects of drugs on the association of beta-arrestin with a GPCR

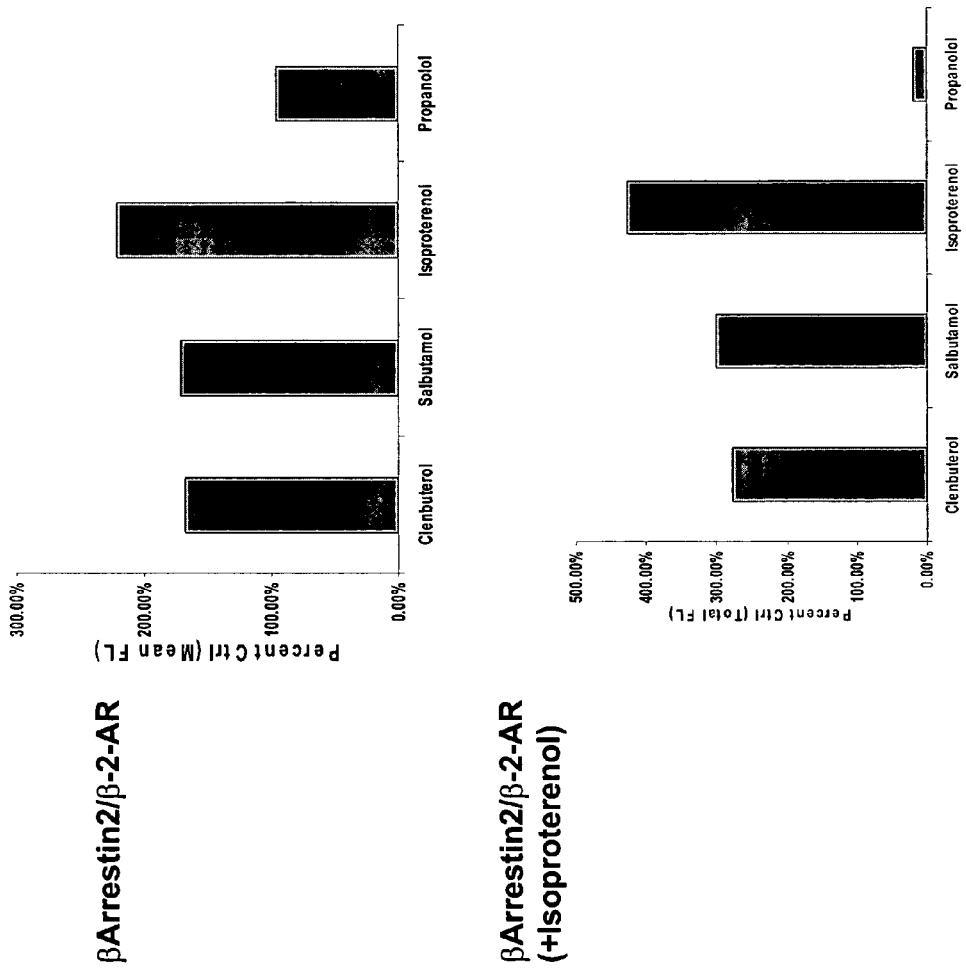
Fig. 9 Quantitation of the effects of drugs on the association of beta-2-adrenergic receptor with beta-arrestin2

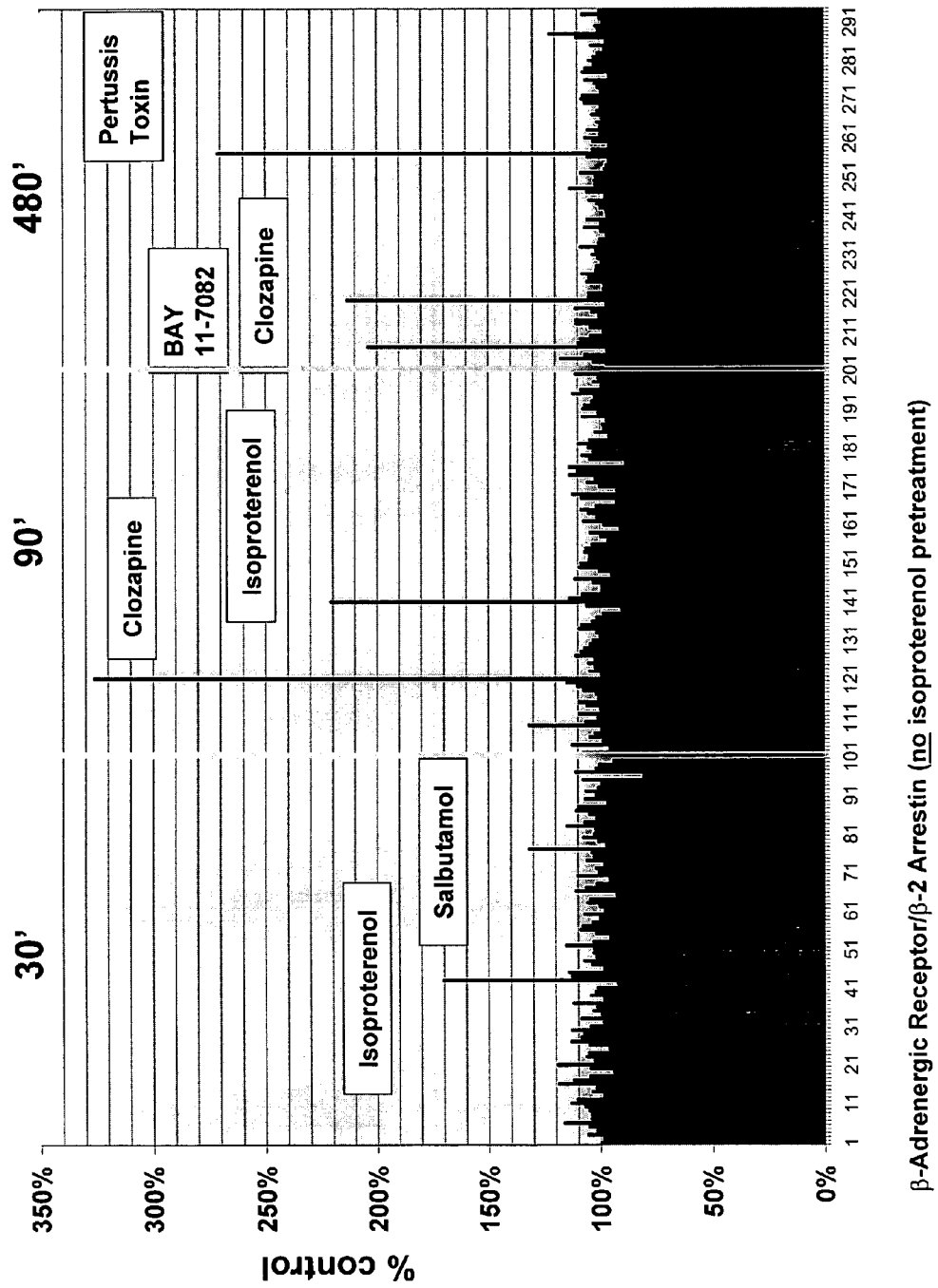
Fig. 10 Screening for GPCR activation using cell-based assays, showing drug effects at early and late time points

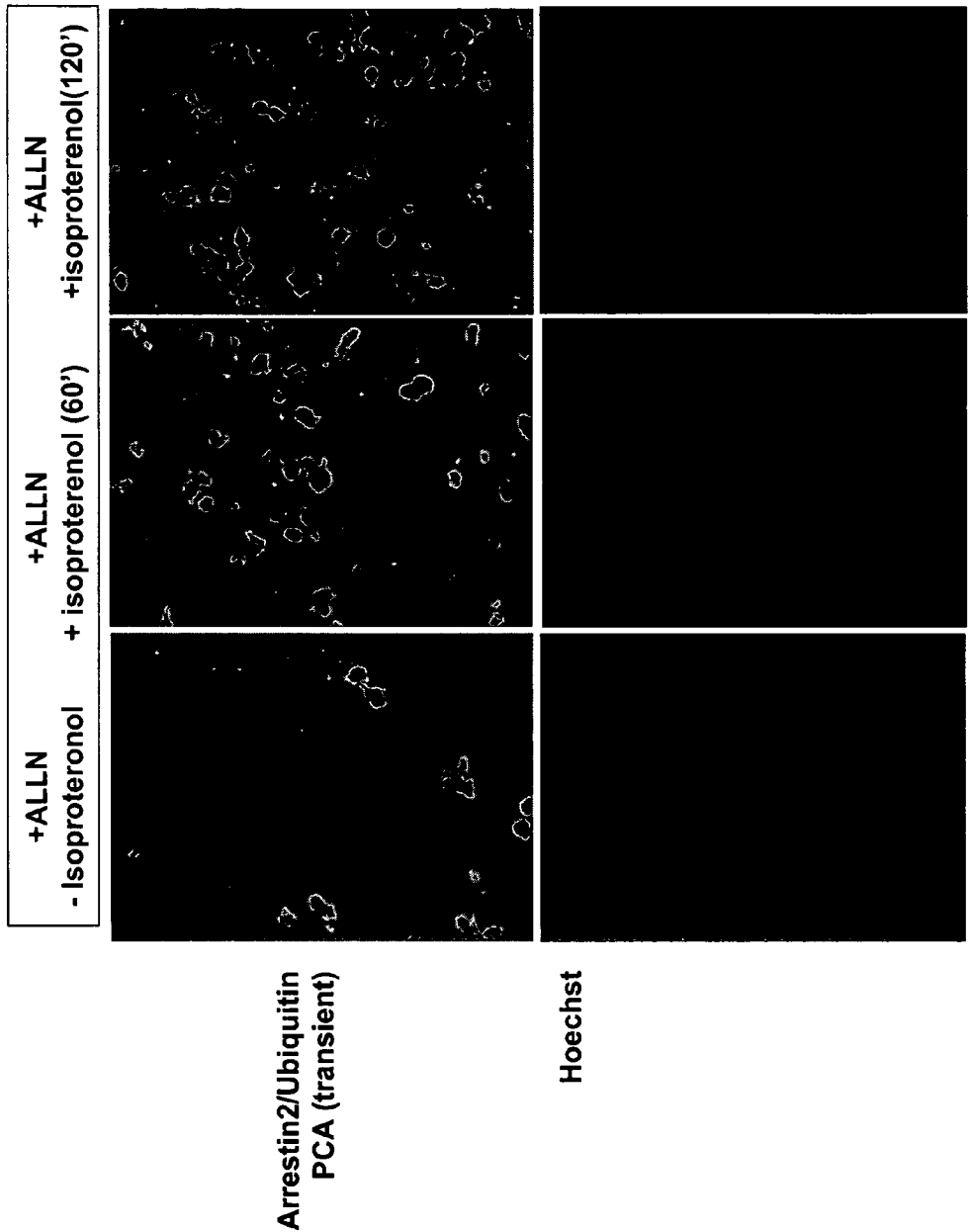
Fig. 11 Proteasomal regulation of GPCR pathways

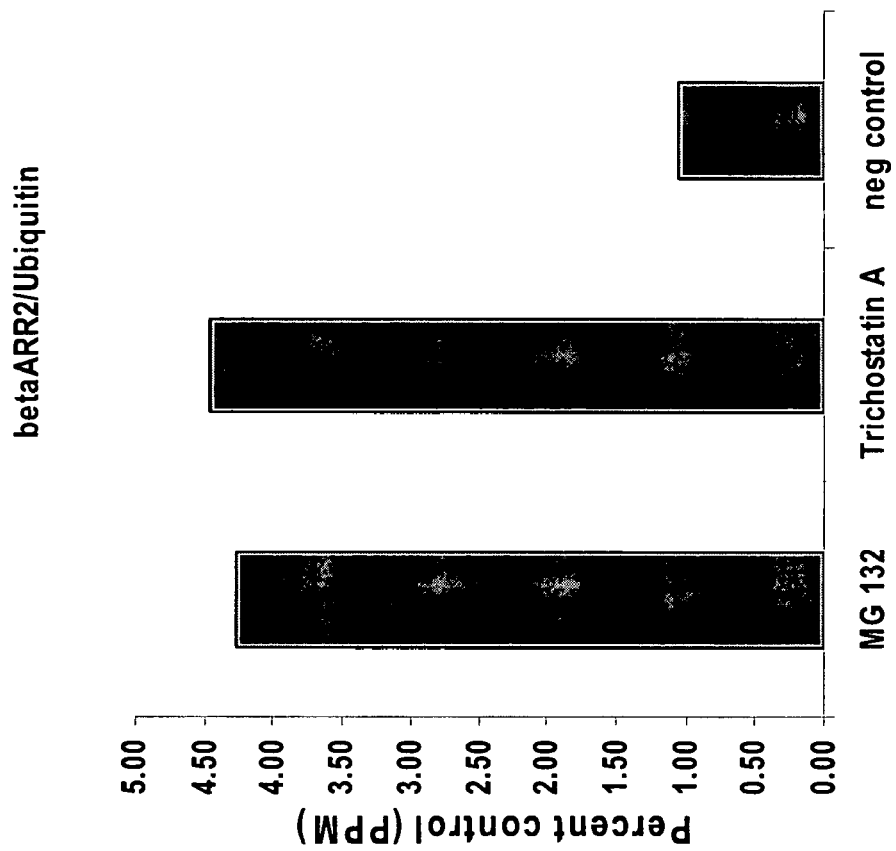
Fig. 12 Demonstration of drug effects in cellular assays: effects of proteasome inhibitors and histone deacetylase inhibitors

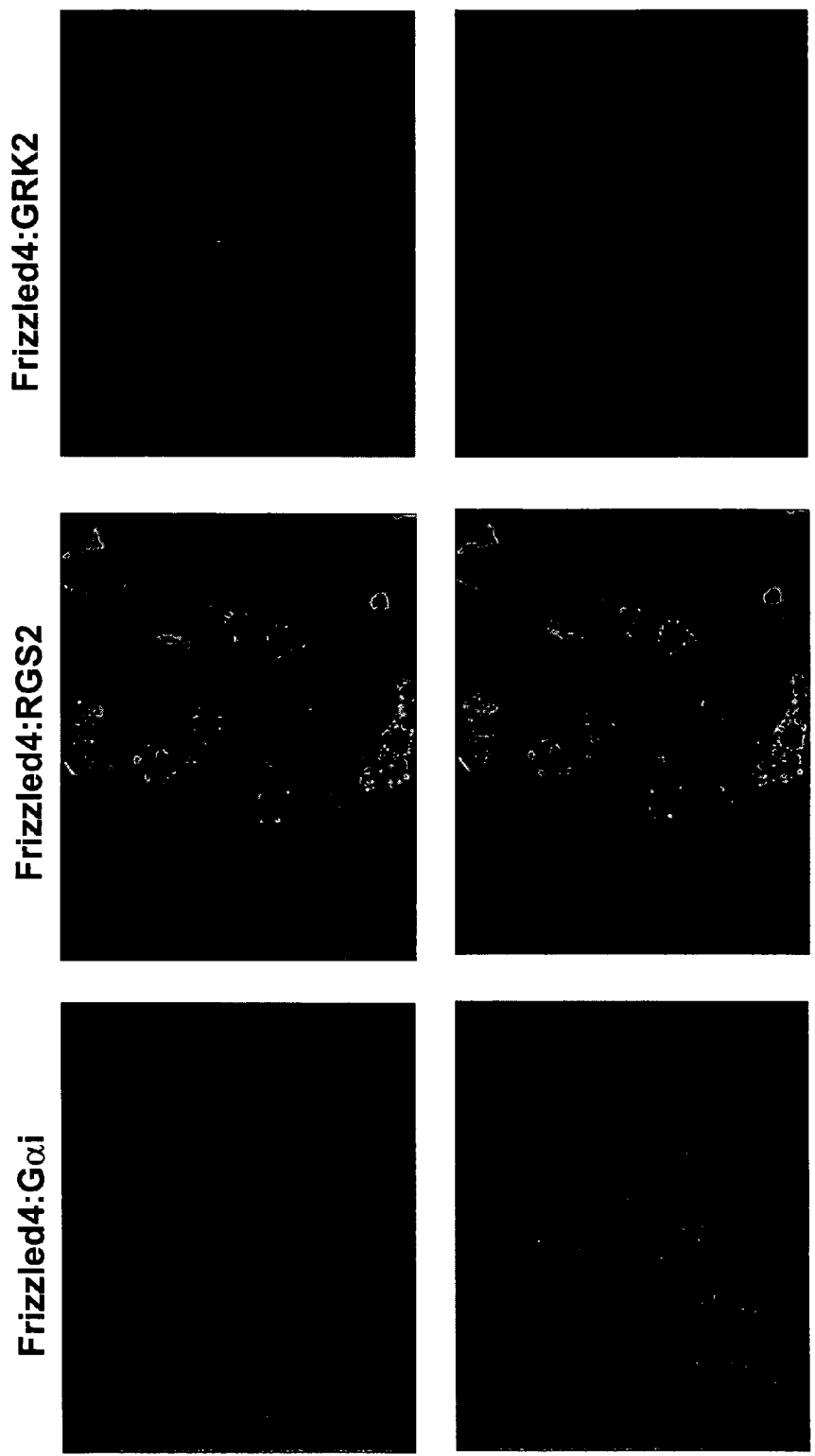
Fig. 13A Novel cell-based assays for GPCR pathways

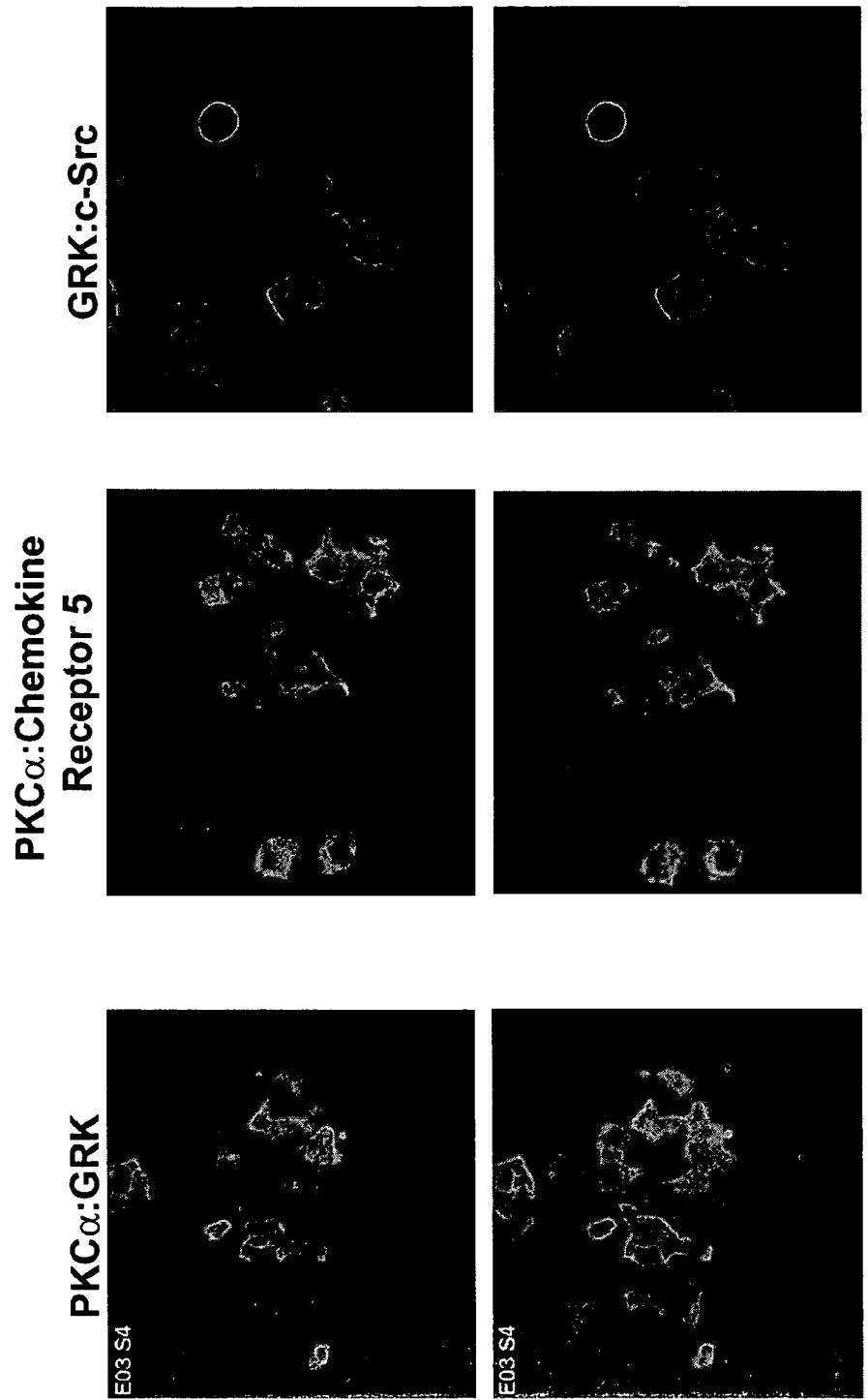
Fig. 13B  Novel cell-based assays for GPCR pathways (continued)

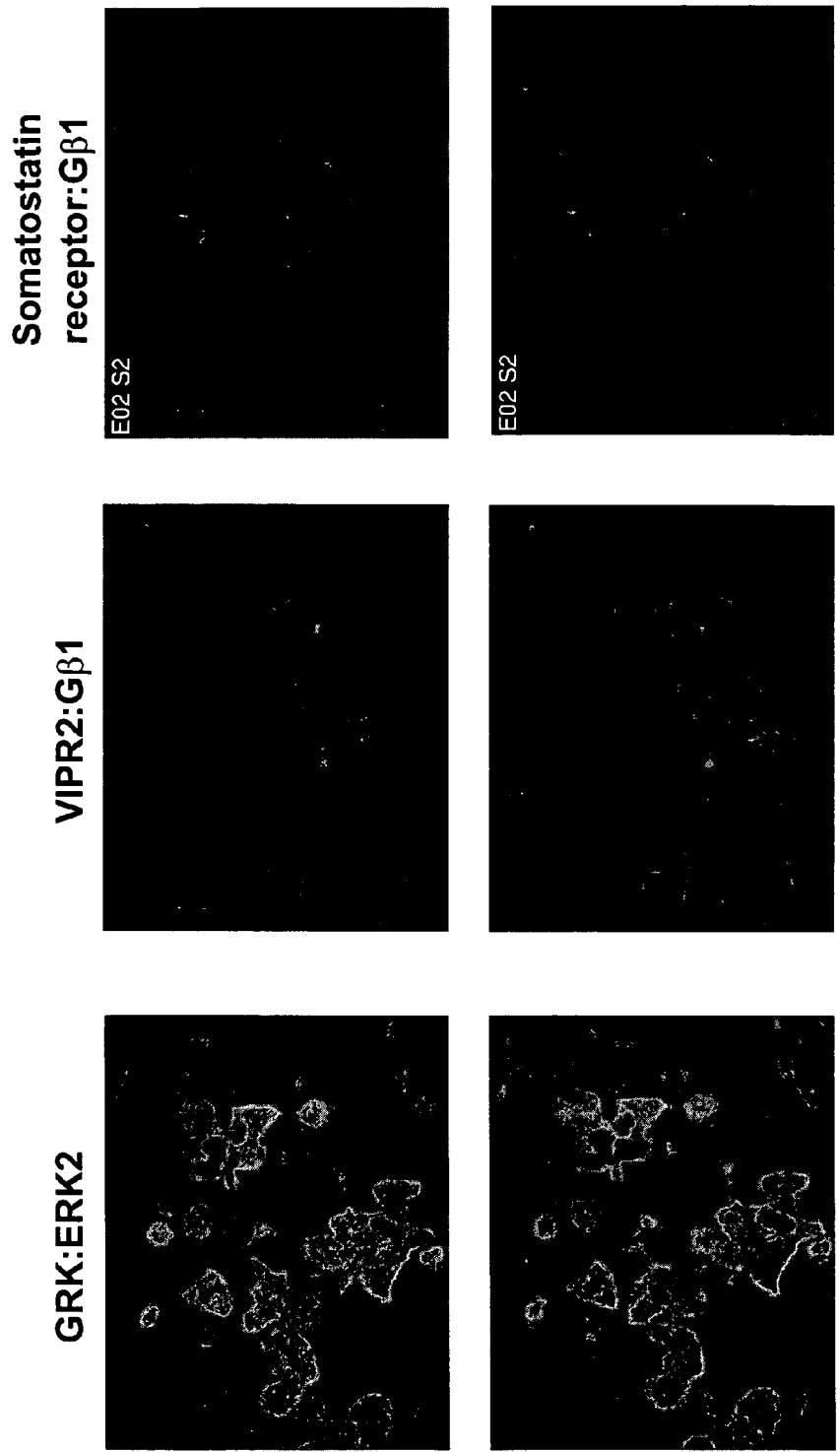
Fig. 13C  Novel cell-based assays for GPCR pathways (continued)
VIPR2= vasoactive intestinal peptide receptor 2

SEQUENCE LISTING

```
<160> NUMBER OF SEQ ID NOS: 6

<210> SEQ ID NO 1
<211> LENGTH: 477
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(477)

<400> SEQUENCE: 1 atg gtg agc aag ggc gag gag ctg ttc acc ggg gtg gtg ccc atc ctg       48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc       96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
        50                  55                  60 ttc ggc tac ggc ctg cag tgc ttc gcc cgc tac ccc gac cac atg aag      240
Phe Gly Tyr Gly Leu Gln Cys Phe Ala Arg Tyr Pro Asp His Met Lys
65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag      336
```

```
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140 aac tac aac agc cac aac gtc tat atc atg gcc gac aag cag taa          477
Asn Tyr Asn Ser His Asn Val Tyr Ile Met Ala Asp Lys Gln
145                 150                 155

<210> SEQ ID NO 2
<211> LENGTH: 158
<212> TYPE: PRT
<213> ORGANISM: Artificial
<220> FEATURE:
<223> OTHER INFORMATION: Synthetic Construct

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln
145                 150                 155

<210> SEQ ID NO 3
<211> LENGTH: 246
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(246)

<400> SEQUENCE: 3 aag aac ggc atc aag gtg aac ttc aag atc cgc cac aac atc gag gac      48
Lys Asn Gly Ile Lys Val Asn Phe Lys Ile Arg His Asn Ile Glu Asp
1               5                   10                  15 ggc agc gtg cag ctc gcc gac cac tac cag cag aac acc ccc atc ggc      96
Gly Ser Val Gln Leu Ala Asp His Tyr Gln Gln Asn Thr Pro Ile Gly
            20                  25                  30 gac ggc ccc gtg ctg ctg ccc gac aac cac tac ctg agc tac cag tcc      144
Asp Gly Pro Val Leu Leu Pro Asp Asn His Tyr Leu Ser Tyr Gln Ser
        35                  40                  45
```

```
gcc ctg agc aaa gac ccc aac gag aag cgc gat cac atg gtc ctg ctg      192
Ala Leu Ser Lys Asp Pro Asn Glu Lys Arg Asp His Met Val Leu Leu
             50                  55                  60 gag ttc gtg acc gcc gcc ggg atc act ctc ggc atg gac gag ctg tac      240
Glu Phe Val Thr Ala Ala Gly Ile Thr Leu Gly Met Asp Glu Leu Tyr
 65                  70                  75                  80 aag taa                                                                246
Lys

<210> SEQ ID NO 4
<211> LENGTH: 81
<212> TYPE: PRT
<213> ORGANISM: Artificial
<220> FEATURE:
<223> OTHER INFORMATION: Synthetic Construct

<400> SEQUENCE: 4

Lys Asn Gly Ile Lys Val Asn Phe Lys Ile Arg His Asn Ile Glu Asp
 1               5                  10                  15

Gly Ser Val Gln Leu Ala Asp His Tyr Gln Gln Asn Thr Pro Ile Gly
                20                  25                  30

Asp Gly Pro Val Leu Leu Pro Asp Asn His Tyr Leu Ser Tyr Gln Ser
             35                  40                  45

Ala Leu Ser Lys Asp Pro Asn Glu Lys Arg Asp His Met Val Leu Leu
         50                  55                  60

Glu Phe Val Thr Ala Ala Gly Ile Thr Leu Gly Met Asp Glu Leu Tyr
 65                  70                  75                  80

Lys

<210> SEQ ID NO 5
<211> LENGTH: 477
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(477)

<400> SEQUENCE: 5 atg gtg agc aag ggc gag gag ctg ttc acc ggg gtg gtg ccc atc ctg       48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc       96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttg atc      144
Glu Gly Glu Gly Asp Ala Thr Tyr Gly Lys Leu Thr Leu Lys Leu Ile
             35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
         50                  55                  60 ctc ggc tac ggc ctg cag tgc ttc gcc cgc tac ccc gac cac atg aag      240
Leu Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110
```

-continued

```
gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
        130                 135                 140 aac tac aac agc cac aac gtc tat atc acg gcc gac aag cag taa          477
Asn Tyr Asn Ser His Asn Val Tyr Ile Thr Ala Asp Lys Gln
145                 150                 155
```

<210> SEQ ID NO 6
<211> LENGTH: 158
<212> TYPE: PRT
<213> ORGANISM: Artificial
<220> FEATURE:
<223> OTHER INFORMATION: Synthetic Construct

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln
145                 150                 155
```

FRAGMENT COMPLEMENTATION ASSAYS FOR G-PROTEIN-COUPLED RECEPTORS AND THEIR SIGNALING PATHWAYS

This application claims the priority benefit under 35 U.S.C. section 119 of U.S. Provisional Patent Application No. 60/505,447 entitled "Fragment Complementation Assays For G-Protein-Coupled Receptors And Their Signaling Pathways", filed Sep. 25, 2003, which is in its entirety herein incorporated by reference.

FIELD OF THE INVENTION

This invention relates generally to the fields of biology, molecular biology, chemistry and biochemistry. The invention is directed to a large number of novel assays for G-protein-coupled receptors (GPCRs) and their signaling pathways. The invention also relates to methods for constructing such assays for one or more steps in a GPCR pathway. The invention can be used for functional characterization of GPCRs, target validation, de-orphanization of receptors, high-throughput screening, high-content screening, pharmacological profiling, and other drug discovery applications. The assays can be used directly to assess whether a compound library or a biological extract contains an agonist or antagonist of a receptor. Assay compositions are also provided. The development of such assays is shown to be straightforward, providing for a broad, flexible and biologically relevant platform for the discovery of novel drugs and natural ligands that act on GPCRs or their cognate pathways. The invention is demonstrated for a broad range of proteins in GPCR pathways and for a range of assay formats.

BACKGROUND OF THE INVENTION

The superfamily of G-protein coupled receptors (GPCRs) represents the largest family of cell surface receptors, and is one of the most important sources of drug targets for the pharmaceutical industry. GPCRs are involved in a wide range of disorders and disease states including ulcers, psychosis, anxiety, Parkinson's disease, Alzheimer's disease and hypertension. More than 20% of the bestselling prescription drugs and an estimated 50% of all prescription drugs interact directly with a GPCR. Also, interactions of drugs with this class of receptors are responsible for some of the side effects associated with these drugs.

Over 500 different GPCRs have been identified in the human genome. As many as 200 of these represent 'orphan' receptors, for which the natural ligand is unknown. The first step for the transformation of orphan receptors into drug targets is their characterization, or 'de-orphanization' (AD Howard et al., 2001, Orphan G-protein-coupled receptors and natural ligand discovery, Trends in Pharmacol. Sci. 22(3): 132-140). De-orphanization of GPCRs, and the identification of synthetic agonists and antagonists, will likely lead to a large number of new and potent medicines for various conditions. This is a task that involves significant efforts, both to understand the potential importance of receptor candidates to specific diseases and to develop efficient drug screening tools. For example, ligands of an identified receptor can be tested against related orphan GPCRs to identify compounds that bind to the orphan receptor. In addition, extracts of tissues can be tested using functional assays to guide ligand fractionation, purification and molecular characterization. Finally, orphan GPCRs can be evaluated against arrayed families of known ligands. Sensitive, biologically relevant assays are needed that can be used to de-orphanize GPCRs on a large scale.

GPCRs do not share any overall sequence homology, but have in common the presence of seven transmembrane-spanning alpha-helical segments connected by alternating intracellular and extracellular loops, with the amino terminus on the extracellular side and the carboxyl terminus on the intracellular side of the cell membrane. Therefore, GPCRs are commonly referred to as seven-transmembrane (7TM) receptors. The GPCRs have been divided into different subfamilies (A-F); the major subfamilies, A, B and C, include the beta-2-adrenergic receptor (family A), receptors related to the glucagon receptor (family B) and receptors related to the neurotransmitter receptors (family C). Family B includes the receptors for vasoactive intestinal peptide, calcitonin, PTH and glucagon; family C includes the receptors for GABA, calcium, mammalian pheromones, and taste receptors. All GPCRs signal through guanine nucleotide-binding proteins (G-proteins). The DNA sequences of a large number of GPCRs can be found in public databases, among other sources (F. Horn et al., 1998, GPCRDB: an Information system for G protein-coupled receptors, Nucleic Acids Res. 26:275-279). The public GPCR database can be found on the worldwide web and corresponding cDNAs and pairwise sequence alignments can also be found on the worldwide web. This database is incorporated herein by reference.

The general mechanism of action of GPCRs in cell signaling has been elucidated over the last 20 years, although many details remain to be discovered. Hundreds of scientific and review articles have been written on the topic (for reviews see GB Downes & N Gautham, 1999, The G-protein subunit gene families, Genomics 62: 544-552; Hermans, 2003, Biochemical and pharmacological control of the multiplicity of coupling at G-protein-coupled receptors, in: Pharmacology & Therapeutics 99: 25-44; and U Gether, 2000, Uncovering molecular mechanisms involved in activation of G-protein-coupled receptors, in: Endocrine Reviews 21: 90-113; E M Hur & K T Kim, 2002, G-protein-coupled receptor signaling and cross talk: achieving rapidity and specificity, Cell Signal 14: 397-405). Some of the known elements of the various G-protein-coupled pathways are described herein for the purposes of placing the present invention in the context of the prior art. Further elucidation of the signaling pathways linked to GPCRs would allow the construction of a large number of assays for intracellular events linked to GPCR activation. In turn, such assays would allow drug discovery to identify drug candidates capable of activating or blocking GPCR signaling.

For drug discovery, there is a need to quickly and inexpensively screen large numbers of chemical compounds to identify new drug candidates, including agonists, antagonists and inhibitors of GPCRs and GPCR-dependent pathways. These chemical compounds are collected in large libraries, sometimes exceeding one million distinct compounds. The use of the term chemical compound is intended to be interpreted broadly so as to include, but not be limited to, simple organic and inorganic molecules, proteins, peptides, antibodies, nucleic acids and oligonucleotides, carbohydrates, lipids, or any chemical structure of biological interest. Traditional, biochemical approaches to assaying GPCRs have relied upon measurements of ligand binding, for example with scintillation proximity assays or with surface plasmon resonance (C. Bieri et al., 1999, Micropatterned immobilization of a G-protein-coupled receptor and direct detection of G protein activation, Nature Biotech. 17: 1105-1109). Although such assays are inexpensive to perform, they can take 6 months or longer to develop. A major problem is that the development of an in vitro assay requires specific reagents for every target of interest, including purified protein for the target against which the screen is to be run. Often it is difficult to express the protein of interest and/or to obtain a sufficient quantity of the protein in pure form. Moreover, although in vitro assays are the gold standard for pharmacology and studies of structure activity relationships (SAR) it is not possible to perform target validation with an in vitro assay, in vivo assays are necessary in order to obtain information about the biological availability and cellular activity of the screening hit.

The increased numbers of drug targets identified by genomics approaches has driven the development of 'gene to screen' approaches to interrogate poorly defined targets, many of which rely on cellular assay systems. Speculative targets are most easily screened in a format in which the target is expressed and regulated in the biological context of a cell, in which all of the necessary components are pre-assembled and regulated. Cell-based assays are also critical for assessing the mechanism of action of new biological targets and the biological activity of chemical compounds. In particular, there is a need to 'de-orphanize' those GPCRs for which the natural activating ligand has not been identified. Various approaches to de-orphanization have been reviewed (A D Howard et al., 2001, Orphan G-protein-coupled receptors and natural ligand discovery, Trends in Pharmacological Sciences 22: 132-140). For example, extracts of tissues can be tested using functional assays to guide ligand fractionation, purification and molecular characterization. Alternatively, orphan GPCRs can be evaluated against arrayed families of known ligands.

Current cell-based assays for GPCRs include measures of pathway activation (Ca2+ release, cAMP generation, or transcriptional activity); measurements of protein trafficking by tagging GPCRs and downstream elements with GFP; and direct measures of interactions between proteins using fluorescence resonance energy transfer (FRET) or bioluminescence resonance energy transfer (BRET) or yeast two-hybrid approaches (e.g. King et al., U.S. Patent Application 20020022238). These approaches are described below.

The majority of cell-based assays for GPCRs rely upon measurements of intracellular calcium. Calcium release from intracellular stores is stimulated by specific classes of GPCRs upon their activation; in particular, those GPCRs that couple to Gq. Fluorescent and luminescent assays of calcium release have been generated by loading cells with dyes that act as calcium indicators. Fluorescent Ca2+ indicators such as fura-2, indo-1, fluo-3, and Calcium-Green have been the mainstay of intracellular Ca2+ measurement and imaging (see for example U.S. Pat. Nos. 4,603,209 and 5,049,673). Such indicators and associated instrumentation systems (FLIPR system) are sold, for example, by Molecular Devices of Sunnyvale Calif. (www.moleculardevices.com). Luminescent assays of calcium flux can be accomplished by introducing aequorin into cells. Aequorin emits blue light in the presence of calcium, and the rate of photon emission is proportional to the free Ca2+ concentration within a specific range. Cells expressing the GPCR of interest are loaded first with coelenterazine to activate the aequorin, and then the compounds to be tested are added to the cells and the results quantitated with a luminometer. To extend these assays to non-Gq-coupled receptors, various strategies have been employed, including the use of a promiscuous Gα protein such as Gα16 that is capable of coupling a wide range of GPCRs to phospholipase C (PLC) activity and calcium mobilization (Milligan et al., 1996, Trends in Pharmacological Sciences 17: 235-237).

Fluorescent dyes, and fluorescent proteins such as GFP, YFP, BFP and CFP, have also been used as cellular sensors of cAMP or Ca2+. The first fluorescent protein indicator for cAMP consisted of the cyclic AMP-dependent protein kinase, PKA, in which the catalytic and regulatory subunits were labelled with fluorescein and rhodamine, respectively, so that cAMP-induced dissociation of the subunits disrupted FRET (S. R. Adams et al., 1991, Fluorescence ratio imaging of cyclic AMP in single cells, Nature 349: 694-697). Replacement of the dyes by GFP and BFP made this system genetically encodable and eliminated the need for in vitro dye conjugation and microinjection (M. Zaccolo et al., 2000, A genetically encoded fluorescent indicator for cyclic AMP in living cells, Nature Cell Biol. 2: 25-29). A variety of other GFP-based techniques have been used to create cellular sensors. For example, two GFP molecules joined by the kinase inducible domain (KID) of the transcription factor CREB (cyclic AMP-responsive element binding protein) exhibit a decrease in fluorescence resonance energy transfer upon phosphorylation of the KID by the cyclic AMP-dependent protein kinase, PKA (Y. Nagai et al., 2000, A fluorescent indicator for visualizing cAMP-induced phosphorylation in vivo, Nature Biotech. 18: 313-316). Calmodulin, a calcium-sensitive protein, has been inserted into YFP, resulting in calcium sensors ('camgaroos') that increase fluorescence sevenfold upon binding of calcium (G S Baird et al., 1999, Circular permutation and receptor insertion within green fluorescent proteins, Proc. Natl. Acad. Sci. USA 96: 11241-11246). Similarly, insertion of a circularly permuted GFP between calmodulin and M13—a peptide that binds calmodulin in a calcium-sensitive manner—yields calcium indicators that are known as 'pericams' (T. Nagai et al., 2001, Circularly permuted green fluorescent proteins engineered to sense Ca2+, Proc. Natl. Acad. Sci USA 98: 3197-3202). Alternative calcium indicators known as 'cameleons' have been created by sandwiching calmodulin, a peptide linker, and M13 between CFP and YFP (A. Miyawaki et al., 1997, Fluorescent indicators for Ca2+ based on green fluorescent proteins and calmodulin, Nature 388: 882-887).

Transcriptional reporter assays provide a measurement of pathway activation/inhibition in response to an agonist/antagonist and have been used extensively in GPCR studies (see Klein et al., U.S. Pat. No. 6,255,059 and references therein). Reporter assays couple the biological activity of a receptor to the expression of a readily detected enzyme or protein reporter. Synthetic repeats of a particular response element can be inserted upstream of the reporter gene to regulate its expression in response to signaling molecules generated by activation of a specific pathway in a live cell. Such drug screening systems have been developed with a variety of enzymatic and fluorescent reporters, including β-galactosidase (H Brauner-Osborne & M R Brann, 1996, Eur. J. Pharmacol. 295: 93-102), luciferase, alkaline phosphatase, GFP, β-lactamase (G. Zlokarnik et al., 1998, Quantitation of transcription and clonal selection of single living cells with beta-lactamase as reporter, Science 279: 84-88) and other reporters. Transcription reporter assays are highly sensitive screening tools; however, they do not provide information on the mechanism of action of the compound, enable mapping of the components of the pathway leading to transcription, or enable studies of individual steps within signaling cascades.

Subcellular compartmentalization of signaling molecules is an important phenomenon in cell signaling, not only in defining how a biochemical pathway is activated but also in influencing the desired physiological consequence of pathway activation. High-content screening (HCS) is an approach that relies upon imaging of cells to detect the subcellular location and trafficking of proteins in response to stimuli or inhibitors of cellular processes. Fluorescent probes can be used in HCS. For example, GTP has been labeled with the fluorescent dye, BODIPY, and used to study the on and offrates of GTP hydrolysis by G-proteins, and fluorescein-labeled myristoylated Galpha-I has been used as the ligand bound to Gbeta-gamma in order to study the association and dissociation of G-protein subunits (N A Sarvazyan et al., 2002, Fluorescence analysis of receptor-G protein interactions in cell membranes, Biochemistry 41: 12858-12867).

Increasingly, green fluorescent protein (GFP) has been used to analyze key signaling events within cells. By fusing in-frame a cDNA for GFP to a cDNA coding for a protein of interest, it is possible to examine the function and fate of the resulting chimera in living cells. This strategy has now been applied to nearly all known elements of G-protein coupled pathways including the receptors themselves; G-protein subunits such as Gα; beta-arrestin; RGS proteins; protein kinase C; and numerous other intracellular components of G-protein-coupled pathways (M Zaccolo and T. Pozzan, 2000, Imaging signal transduction in living cells with GFP-based probes, IUBMB Life 49: 1-5, 2000.)

For example, G-protein-coupled receptors have been tagged with GFP in order to monitor receptor internalization. A fusion protein comprising GFP-beta-arrestin has been shown to co-localize with thyrotropin-releasing hormone receptor 1 in response to agonist (T Drmota et al., 1999, Visualization of distinct patterns of subcellular redistribution of the thyrotropin-releasing hormone receptor-1 and Gqalpha/G11alpha induced by agonist stimulation, Biochem. J. 340: 529-538). GFP has been introduced internally to G-proteins, creating a Galpha/GFP chimera, which has been shown to translocate to the cell membrane upon GPCR activation (J-Z Yu & M Rasenick, 2002, Real-time visualization of a fluorescent GalphaS dissociation of the activated G protein from plasma membrane, Mol. Pharmacol. 61: 352-359; P Coward et al., 1999, Chimeric G proteins allow a high-throughput signaling assay of Gi-coupled receptors, Anal. Biochem. 270: 242-248). GFP tagging has also been used to monitor intracellular signaling events. GFP-tagged Regulator of G protein Signaling (RGS2 and RGS4) proteins were selectively recruited to the plasma membrane by G proteins and their cognate receptors (A A Roy et al., 2003, Recruitment of RGS2 and RGS4 to the plasma membrane by G proteins and receptors reflects functional interactions. Mol. Pharmacol. 64: 587-593). GFP-tagged protein kinase C (PKC), which is activated by release of diacylglycerol from cell membranes, has been used to monitor translocation of the kinase in response to cell signaling (E. Oancea et al., 1998, Green fluorescent protein (GFP)-tagged cysteine-rich domains from protein kinase C as fluorescent indicators for diacylglycerol signaling in living cells, J. Cell Biol. 140: 485-498). GFP-tagged connexin has been used to monitor intracellular calcium flux (K Paemeleire et al., 2000, Intercellular calcium waves in HeLa cells expressing GFP-labeled connexin, Mol. Biol. Cell 11: 1815-1827). GFP-tagged beta-arrestin has been used to monitor GPCR activation by imaging the subcellular redistribution of beta-arrestin in reponse to GPCR agonist. The latter assay, known as TransFluor, is marketed by Norak Bioscience (www.norakbio.com) and is the subject of U.S. Pat. Nos. 5,891,646 and 6,110,693. All the above assays and inventions involve fusing a protein of interest (receptor, beta-arrestin, G-protein, connexin, RGS, kinase etc.) to an optically detectable molecule such as GFP; expressing the fusion construct in cells; and then detecting the quantity, and/or the subcellular location, of the chimeric protein in response to a stimulus or inhibitor.

Measurements of protein-protein interactions between GPCRs and cognate intracellular signaling proteins represent an alternative to the above-mentioned techniques. In contrast to monitoring a single protein by tagging it with GFP, a protein-protein interaction assay is capable of measuring the dynamic association and dissociation of two proteins. The most widespread cell-based assays for protein-protein interactions are based on fluorescence resonance energy transfer (FRET) or bioluminescence resonance energy transfer (BRET). With FRET, the genes for two different fluorescent protein reporters are separately fused to genes encoding of interest, and the two chimeric proteins are co-expressed in live cells. When a protein complex forms between two proteins of interest, the two fluorophores are brought into close proximity. If the two proteins possess overlapping emission and excitation wavelengths, the emission of photons by the first "donor" fluorophore, results in the efficient absorption of the emitted photons by the second "acceptor" fluorophore. The FRET pair fluoresces with a unique combination of excitation and emission wavelengths that can be distinguished from those of either fluorophore alone in living cells. Quantifying FRET or BRET can be technically challenging its use in imaging protein-protein interactions is limited by the very weak FRET signal. The signal is often weak because the acceptor fluorophore is excited only indirectly, through excitation of the donor. The fluorescence wavelengths of the donor and acceptor must be quite close for FRET to work, because FRET requires overlap of the donor emission and acceptor excitation. Newer methods are in development to enable deconvolution of FRET from bleed-through and from autofluorescence. In addition, fluorescence lifetime imaging microscopy eliminates many of the artifacts associates with quantifying simple FRET intensity.

For example, FRET has been used to study GPCR-mediated activation of G-proteins in living cells (C. Janetopoulos, 2001, Receptor-mediated activation of heterotrimeric G-proteins in living cells, Science 291:2408-2411) and to study the association of PKA with AKAPs (M L Ruehr et al., 1999, Cyclic AMP-dependent protein kinase binding to A-kinase anchoring proteins in living cells by fluorescence resonance energy transfer of green fluorescent protein fusion proteins, J. Biol. Chem. 274: 33092-33096). A variety of GFP variants, including cyan, citrine, enhanced green and enhanced blue fluorescent proteins, have been used to construct FRET assays. With BRET, a luminescent protein, such as the enzyme Renilla luciferase (Rluc) is used as the energy donor and a green fluorescent protein (GFP) is used as the acceptor. Upon addition of a compound that serves as the substrate for Rluc, the FRET signal is measured by comparing the amount of blue light emitted by Rluc to the amount of green light emitted by GFP. The ratio green/blue ratio increases as the two proteins are brought into proximity. FRET and BRET have been applied to studies of GPCR oligomerization for oligomers of the β2-adrenergic, δ-opioid, thyrotropin releasing hormone and melatonin receptors. BRET has also been used for studies of the agonist-dependent association of beta2-arrestin with the beta2-adrenergic receptor in live cells (S Angers et al., 2000, Detection of beta-2-adrenergic receptor dimerization in living cells using bioluminescence resonance energy transfer, Proc. Natl. Acad. Sci. USA 97: 3684-3689). Receptor ligands, coupled to fluorophores, have also been used as FRET partners to monitor oligomerization of GPCRs.

In principle, cell-based assays of protein-protein interactions can be used both to monitor the activity of a biochemical pathway in the living cell and to directly study the effects of chemicals on targets and pathways. Unlike transcriptional reporter assays, the information obtained from perturbation of a specific pathway is what is happing specifically in a particular branch or node of that pathway, not its endpoint. Protein-fragment complementation assays (PCAs) and enzyme-fragment complementation assays represent an alternative to FRET-based methods. PCA involves tagging of proteins with polypeptide fragments derived by fragmenting a suitable reporter. Unlike intact fluorescent proteins or holoenzymes, the PCA fragments have no intrinsic activity or fluorescence. However, if two proteins that are tagged with complementary fragments interact, the fragments are brought into close proximity. The complementary fragments can then fold into an active conformation and re-constitute the activity of the reporter from which the fragments were derived. Unlike FRET or BRET, PCA-based fluorescent or luminescent assays provide for signals with large dynamic range. Moreover, PCAs do not require specialized optics or equipment. Using a similar approach, naturally-occurring subunits of a multimeric protein—beta-galactosidase—have been used to construct complementation assays for the measurement of protein-protein interactions (Rossi, et al., 1997, Monitoring protein-protein interactions in intact eukaryotic cells by beta-galactosidase complementation. *Proc Natl Acad Sci USA* 94: 8405-8410).

Fluorescent PCAs based either on dihydrofolate reductase or beta-lactamase have been used to quantify the effects of the drug rapamycin on its target in living cells (Remy, I. and Michnick, S. W., Clonal Selection and In Vivo Quantitation of Protein Interactions with Protein Fragment Complementation Assays. Proc Natl Acad Sci USA, 96: 5394-5399, 1999; Galameau, A., Primeau, M., Trudeau, L.-E. and Michnick, S. W., A Protein fragment Complementation Assay based on TEM1 β-lactamase for detection of protein-protein interactions, Nature Biotech. 20: 619-622, 2002 and to study phosphorylation-dependent interactions of two domains of the cyclic AMP response element binding protein, CREB (J M Spotts, R E Dolmetsch, & M E Greenberg, 2002, Time-lapse imaging of a dynamic phosphorylation-dependent protein-protein interaction in mammalian cells, Proc. Natl. Acad. Sci. USA 99: 15142-15147.) PCA has also been used to construct quantitative and high-content assays for a variety of proteins in the insulin and growth factor-dependent pathways in mammalian cells (Remy, I. and Michnick, S. W., Visualization of Biochemical Networks in Living Cells, Proc Natl Acad Sci USA, 98: 7678-7683, 2001 and U.S. Patent Application 20030108869).

With regard to direct assays of receptor activation, PCA has been used to construct fluorescent assays of the erythropoietin (EPO) receptor in living cells (Remy, I., Wilson, I. A. and Michnick, S. W., Erythropoietin receptor activation by a ligand-induced conformation change, Science 283: 990-993, 1999; Remy, I. and Michnick, S. W., Clonal selection and in vivo quantitation of protein interactions with protein fragment complementation assays, Proc Natl Acad Sci USA, 96: 5394-5399, 1999; and U.S. Pat. No. 6,294,330). These assays were quantitative, demonstrating dose dependence and showing a differential response to erythropoietin or EMP1 consistent with the EC50 of the two agonists. Similarly, enzyme-fragment complementation assays based on low-affinity subunits of β-galactosidase have been used to study EGF receptor dimerization in living cells (Rossi, et al., Monitoring protein-protein interactions in intact eukaryotic cells by beta-galactosidase complementation, Proc Natl Acad Sci USA 94: 8405-8410, 1997; and U.S. Pat. No. 6,342,345). However, the prior art is silent on the use of either protein-fragment or enzyme-fragment complementation assays for G-protein-coupled receptors or G-protein-coupled signaling pathways.

At its basic level, fragment complementation is a general and flexible strategy that allows measurement of the association and dissociation of protein-protein complexes in intact, living cells. In particular, PCA has unique features that make it an important tool in drug discovery:

Molecular interactions are detected directly, not through secondary events such as transcription activation or calcium release.

Tagging of proteins with large molecules, such as intact, fluorescent proteins, is not required.

With in vivo PCAs, proteins are expressed in the relevant cellular context, reflecting the native state of the protein with the correct post-translational modifications and in the presence of intrinsic cellular proteins that are necessary, directly or indirectly, in controlling the protein-protein interactions that are being measured by the PCA.

PCA allows a variety of reporters to be used, enabling assay design specific for any instrument platform, automation setup, cell type, and desired assay format. Reporters suitable for PCA include fluorescent, phosphorescent and luminescent proteins (GFP, YFP, CFP, BFP, RFP and variants thereof, and photoproteins (aequorin or obelin); various luciferases; β-lactamase; dihydrofolate reductase; beta-galactosidase; tyrosinase; and a wide range of other enzymes.

Depending upon the choice of reporter, either high-content or high-throughput assays can be constructed with PCA, allowing flexibility in assay design depending on the specific target and the way in which it responds to agonist or antagonist in the cellular context.

With high-content PCAs, the sub-cellular location of protein-protein complexes can be determined, whether in the membrane, cytoplasm, nucleus or other subcellular compartment; and the movement of protein-protein complexes can be visualized in response to a stimulus or inhibitor.

With high-throughput PCAs, the assays are quantitative and can be performed either by flow cytometry or in multi-well, microtiter plates using standard fluorescence microplate readers.

PCA can be used to 'map' proteins into signaling pathways and validate novel targets by detecting the interactions that a particular protein makes with other proteins in the context of a mammalian cell, and then determining whether the protein-protein complex can be modulated in response to an agonist, antagonist or inhibitor.

OBJECTS AND ADVANTAGES OF THE INVENTION

It is an object of the present invention to provide methods for functional annotation and screening of GPCRs and GPCR-dependent pathways on a large scale. It is an object of this invention to allow the rapid construction of screening assays for GPCRs, starting with genes encoding the receptors or their downstream signaling elements. Another object of this invention is to enable either high-throughput assays or high-content assays for GPCRs and GPCR-dependent pathways. A further object of this invention is to provide compositions useful for such assays, including suitable signaling proteins that can be used in assay construction. It is also an object of this invention to provide for a variety of detection options, including fluorescent, luminescent, phosphorescent or colorimetric readouts. Advantages of the invention include the ability to screen for agonists, antagonists and inhibitors for any GPCR or GPCR-dependent pathway, in any cell type of interest. Another advantage of the invention is the ability to de-orphanize GPCRs for drug discovery. A further advantage is the ability to construct assays suitable for a wide range of detection methods, laboratory instrumentation and automa-

SUMMARY OF THE INVENTION

The present invention seeks to provide the above-mentioned needs for drug discovery. The present invention provides a general strategy for constructing and employing high-throughput assays for GPCRs and GPCR-dependent pathways based on reporter complementation strategies, including protein-fragment complementation assays (PCAs) and enzyme-fragment complementation assays. The present invention also teaches how such assays can be applied to de-orphanization of receptors, mapping of pathways, and screening of compound libraries in order to identify natural products, small molecules, peptides, nucleic acids, or other pharmacologically active agents that can inhibit or activate specific biochemical pathways in live cells.

The present application teaches general approaches to developing a GPCR assay, including methods for identifying and selecting an interacting protein pair for the construction of assays for GPCRs and G-protein-coupled signaling pathways. Multiple methods for identifying or selecting an interacting protein pair are described, including cDNA library screening, gene-by-gene interaction mapping. These methods can be used to map the intracellular signaling elements linked to a specific GPCR, thereby generating additional assays for drug screening. Prior knowledge or hypothesis regarding a pathway or a protein-protein interaction can also be used to design and construct such assays.

Methods and compositions are provided both for high-throughput screens (HTS) and for high-content screens (HCS). These assays can be used for the screening of compound libraries to identify compounds of potential therapeutic value, and for the screening of biological compounds or extracts for natural ligands. These assays can be used to identify the native ligand of a GPCR (de-orphanization) and to identify the signaling pathway(s) for 'orphan' GPCRs. Signals that are optically detectable in live cell assays, such as fluorescence, luminescence or phosphorescence, can be generated. Cell lysates and fixed cells can also be used in the present invention. Cell fixation offers advantages over live cell assays for purposes of laboratory automation, since entire assay plates can be fixed at a specific time-point after cell treatment, loaded into a plate stacker or carousel, and read at a later time. Alternatively, in vitro assays can be constructed using the strategies and methods described herein. While in vitro assays have the disadvantage of being de-coupled from live-cell signaling events, they may offer certain advantages for ultra high-throughput, low-cost screening.

In the case of purely quantitative assays, the signal generated in the assay is quantified with a microtiter fluorescence plate reader, flow cytometer, fluorimeter, microfluidic device, or similar devices. The intensity is a measure of the quantity of the protein-protein complexes formed and allows for the detection of changes in protein-protein complex formation in live cells in response to agonists, antagonists and inhibitors. In the case of high-content assays, cells are imaged by automated microscopy, confocal, laser-based, or other suitable high-resolution imaging systems. The total fluorescence/cell as well as the sub-cellular location of the signal (membrane, cytosol, nucleus, endosomes, etc.) can be detected. The choice of HTS or HCS formats is determined by the biology and biochemistry of the signaling event and the functions of the proteins being screened. It will be understood by a person skilled in the art that the HTS and HCS assays that are the subject of the present invention can be performed in conjunction with any instrument that is suitable for detection of the signal that is generated by the chosen reporter.

The general characteristics of reporters suitable for PCA, methods of engineering reporters for PCA, and various uses of PCA, have been described in detail (U.S. Pat. No. 6,270,964 which is incorporated herein by reference). Examples of reporters suitable for the present invention are shown in Table I. The present invention teaches that any reporter suitable for PCA can be utilized to create an assay for a GPCR or a G-protein-coupled pathway. The present application also explains the rationale for selecting a particular reporter. Preferred embodiments of the invention include the creation of assays based on fragments of the following reporters (see Table 1): beta-lactamase; beta-galactosidase; Gaussia, *Renilla* or firefly luciferase; yellow fluorescent protein; the YFP mutant known as Venus; kindling fluorescent protein; (KFP1); photoactivatable GFP (PA-GFP); aequorin; and obelin. Alternate embodiments of the invention include the following reporters: dihydrofolate reductase; cyan fluorescent protein; monomeric red fluorescent protein; a large number of alternative PCA reporters that have been described by Michnick et al. (U.S. Pat. No. 6,270,964) and in Table 1; and the split ubiquitin and split intein systems (J. N. Pelletier, I. Remy and S. W. Michnick (1998) Protein-Fragment Complementation Assays: a General Strategy for the in vivo Detection of Protein-Protein Interactions. *Journal of Biomolecular Techniques*, accession number S0012; T. Ozawa, T M Takeuchi, A. Kaihara, M. Sato and Y. Umezawa (2001) Protein splicing-based reconstitution of split green fluorescent protein for monitoring protein-protein interactions in bacteria: improved sensitivity and reduced screening time. (2001) Anal. Chem. 73: 5866-5874) which rely upon DHFR, GFP or similar proteins to generate an optically detectable signal.

TABLE 1

Examples of reporters suitable for the present invention

| Protein | Nature of Signal | Reference |
| --- | --- | --- |
| Aequorin monomeric calcium activated photoprotein | Luminescence, requires cell permeable coelenterazine luciferin and calcium | Ungrin et. al. (1999) An automated aequorin luminescence-based functional calcium assay for G-protein-coupled receptors, Anal Biochem. 272, 34-42; Rizzuto et. al. (1992) Rapid changes of mitochondrial calcium revealed by specifically targeted recombinant aequorin, Nature 358 (6384): 325-327 |
| AsFP499 and related fluorescent proteins from the sea anemone Anemonia sulcata | Fluorescence | Weidenmann et al. (2000) Cracks in the beta-can: fluorescent proteins from anemonia Sulcata Proc. Natl. Acad. Sci. USA 97 (26): 14091-14096 |

TABLE 1-continued

Examples of reporters suitable for the present invention

| Protein | Nature of Signal | Reference |
| --- | --- | --- |
| Beta-galactosidase | Fluorescence | Rossi, et al. (1997) Monitoring protein-protein interactions in intact eukaryotic cells by beta-galactosidase complementation. Proc Natl Acad Sci USA 94: 8405-8410. |
| Beta-lactamase | Fluorescence, CCF2/AM or other cell-permeable cephalosporin substrate | Michnick et. al. (2002) Nature Biotechnology 20: 619-622 |
| Blue fluorescent proteins, BFPs | Fluorescence | Pavlakis et. al. Mutant Aequorea victorea fluorescent proteins having increased cellular fluorescence, U.S. Pat. No. 6,027,881 |
| "Citrine" a novel engineered version of YFP | Fluorescence | Griesbeck et. al. (2001) Reducing the environmental sensitivity of yellow fluorescent protein. J. Biol Chem., 31: 29188-29194 |
| Cyan fluorescent protein: ECFP and enhanced GFP and YFP: EGFP, EYFP | Fluorescence | Zhang et al. (2002) Creating new fluorescent probes for cell biology, Nature Reviews Mol. Cell Biology 3:, 906-918; Tsien (1998) Annu. Rev. Biochem. 67: 509-544. |
| Dihydrofolate reductase (DHFR) | Fluorescence, binding of fluorophore-methotrexate to reconstituted DHFR | Remy & Michnick (2001). Visualization of Biochemical Networks in Living Cells. Proc Natl Acad Sci USA, 98: 7678-7683. |
| DsRed a tetrameric red fluorescent protein from discosoma coral | Fluorescence | Matz et al. (1999) Fluorescent proteins from nonbioluminescent anthozoa species. Nature Biotechnology, 17 (10): 969-973 |
| EqFP611 a red fluorescent protein from the sea anemone Entacmaea quadricolor | Fluorescence | Wiedenmann et al. (2002) A far-red fluorescent protein with fast maturation and reduced oligomerization tendency from Entacmaea quadricolor. Proc. Natl. Acad. Sci. USA 99(18): 11646-11651 |
| Firefly luciferase | Luminescence, requires D luciferin | Rutter et al. (1995) Involvement of MAP kinase in insulin signaling revealed by non-invasive imaging of luciferase gene expression in living cells, Current Biology 5 (8): 890-899; De Wet et. al. (1985) Proc. Natl. Acad. Sci., USA 82: 7870-7873; de Wet et. al. (1986) Methods in Enzymology, 133, 3; U.S. Pat. No. 4,968,613. |
| GFP | Fluorescence | Remy et al. (2000) Protein interactions and Library screening with protein fragment complementation strategies, in: Protein-protein interactions: a molecular cloning manual. Cold Spring Harbor Laboratory Press. Chapter 25, 449-475; and U.S. Pat. No. 6,270,964 |
| "Kaede" a new fluorescent protein isolated from coral | Fluorescence; green to red photoconversion | Ando et al. (2002) An optical marker based on the uv-induced green-red photoconversion of a fluorescent protein, Proc. Natl. Acad. Sci. USA 99 (20): 12651-12656 |
| m-RFP monomeric red fluorescent protein derived by engineering DsRed. | Fluorescence | Campbell et al. (2002) A monomeric red fluorescent protein. Proc. Natl. Acad. Sci. USA 99 (12): 7877-7882 |
| Obelin a 22 kd monomeric calcium activated photoprotein | Calcium activated photoprotein also requires coelenterazine luciferin | Campbell et al. (1988) Formation of the calcium activated photoprotein obelin from apo-obelin and mRNA in human neutrophils, Biochem J. 252 (1): 143-149 |
| PA-GFP a new mutant of YFP | Fluorescence; photoactivatable | Patterson et al. (2002) A photoactivatable GFP for selective labeling of proteins and cells. Science 297: 1873-1877. |
| Recombinant monomeric glucuronidases/glycosidases | Fluorescence | Such enzymes can produced either by protein engineering of the subunit interface of existing symmetrical multimeric enzymes or suitable naturally occurring monomeric glycosyl hydrolases and detected using cell permeable fluorescent substrates such as e.g. the lipophilic substrate: ImaGene Green C12 FDGlcU available from Molecular Probes; Catalog number 1-2908 |
| Reef coral Anthozoan derived GFPs | Fluorescence | Labas et al. (2002) Diversity and evolution of the green fluorescent protein family, Proc. Natl. Acad. Sci., USA 99(7): 4256-4262; Matz et al. (1999) Fluorescent proteins from nonbioluminescent anthozoa species. Nature Biotechnology 17 (10): 969-973. |
| Renilla and Ptilosarcus Green fluorescent proteins | Fluorescence | Luciferases, fluorescent proteins, nucleic acids encoding the luciferases and fluorescent proteins and the use thereof in diagnostics, high throughput screening and novelty items. U.S. Pat. No. 6,436,682 B1, Aug. 20, 2002 assigned to Prolume, Ltd. |
| Renilla luciferase. monomeric luminescent photoprotein and | Luminescence. Renilla luciferase requires cell-permeable | Baumik et al. (2002) Optical imaging of renilla luciferase reporter gene expression in living mice, |

TABLE 1-continued

Examples of reporters suitable for the present invention

| Protein | Nature of Signal | Reference |
| --- | --- | --- |
| Firefly luciferase | coelenterazine luciferin. Firefly luciferase requires D-luciferin. | Proc. Natl. Acad. Sci., USA 99 (1): 377-382; Lorenz et al. (1991) Isolation and expression of a cDNA encoding renilla reniformis luciferase, Proc. Natl. Acad. Sci., USA 88: 4438-4442. |
| "Venus" and super-enhanced YFP (SEYFP) | Fluorescence | Nagai et al. (2002) A variant of yellow fluorescent protein with fast and efficient maturation for cell-biological applications. Nature Biotechnology 20: 87-90 |
| Renilla mulleri, Gaussia and Pleuromma luciferases | Luminescence | Luciferases, fluorescent proteins, nucleic acids encoding the luciferases and fluorescent proteins and the use thereof in diagnostics, high throughput screening and novelty items. U.S. Pat. No. 6,436,682 B1, Aug. 20, 2002 |

BRIEF DESCRIPTION OF THE DRAWINGS

FIG. 1 illustrates the general strategy for the design and construction of an assay according to the present invention.

FIG. 2 shows a live cell assay for self-association of a G-protein-coupled receptor.

FIG. 3 shows an assay for the association of a G-protein-coupled receptor with a G-protein α subunit (Gαi) in two different human cell types.

FIG. 4 shows an assay for the association of a G-protein-coupled receptor with a G-protein β subunit (Gβ1)

FIG. 5 shows a quantitative assay for the association of a G-protein-coupled receptor with beta-arrestin, demonstrating an increase in signal intensity in response to agonist.

FIG. 6 shows a time course for the effect of agonist on the association of a G-protein-coupled receptor with beta-arrestin, showing both an increase in signal intensity with time and a redistribution of the protein-protein complex into intracellular granules.

FIG. 7 shows that individual fragment fusions do not generate an optically detectable signal; signal generation depends upon fragment complementation.

FIG. 8 demonstrates the effects of drugs on the association of beta-arrestin2 with the beta-2 adrenergic receptor. In the absence of agonist (upper left panel) there is no YFP signal; only the Hoechst-stained cell nuclei are seen. In the presence of isoproterenol the two proteins associate, causing the reassociation of YFP fragments to generate a bright punctuate fluorescence. The antagonist, propanolol, blocks the effect of isoproterenol. The assay can be used to screen for novel agonists and antagonists of the beta-adrenergic receptor. This assay principle can be applied to any GPCR that binds to an arrestin molecule.

FIG. 9 shows the quantitative results obtained from the assay shown in FIG. 8. Fluorescence intensity of the YFP channel is shown as a percent of control (vehicle alone). The effects of several different agonists (clenbuterol, salbumatomol and isoproterenol) are shown. The antagonist, propanolol, completely blocks the effect of isoproterenol.

FIG. 10 shows the results of using the assay of FIG. 8 to screen for agents that activate the GPCR pathway at different time points. 98 different drugs were tested for their ability to increase the interaction of the beta-adrenergic receptor with beta-arrestin2 at either 30 minutes, 90 minutes or 480 minutes. Fluorescence intensity of the YFP channel is shown as a percent of control (vehicle alone). The direct agonists isoproterenol and salbutamol had effects at early time points whereas other drugs (BAY 11-7082, clozapine and pertussis toxin) had effects only at later time points consistent with their different mechanisms of action.

FIG. 11 shows an assay for the detection of proteasomal regulation of GPCR pathways. The ubiquitination of beta-arrestin2 was measured. Signal was apparent only in the presence of the proteasome inhibitor ALLN (upper left panel). In the presence of ALLN, isoproterenol caused a significant increase in signal at 60' or 120'. These assays can be used to identify novel proteasome inhibitors.

FIG. 12 demonstrates the effects of drugs on the beta-arrestin2-ubiquitin assay. The proteasome inhibitor MG132 and the histone deacetylase inhibitor, Trichostatin A, increased the signal fourfold over the negative control (vehicle alone). Assay fluorescence is shown as a percent of control for the positive pixel mean fluorescence intensity (PPM).

FIG. 13 (A-C) demonstrates a variety of high-content fragment complementation assays for GPCRs and their cognate pathways. Fluorescence micrographs for specific protein-fragment complementation assays are shown. Fluorescence from the Hoechst nuclear staining of HEK cells is in blue whereas the YFP PCA signals from transient transfections are in yellow/green. Subcellular localization of the protein-protein complexes can also be seen. Assays for the following protein-protein pairs are shown: Frizzled4/G-alpha-I; Frizzled 4/RGS2; Frizzled 4/GRK2; PKCalpha/GRK; PKCalpha/Chemokine Receptor 5; GRK/c-Src; GRK/ERK2; VIPR2/G-beta-1; and the Somatostatin Receptor/G-beta-1.

DETAILED DESCRIPTION OF THE INVENTION

Assay Construction

An overview of the process of constructing an assay for a GPCR or a G-protein-coupled pathway is shown in FIG. 1. The genes to be used in the assay may code either for known or for novel interacting proteins. The interacting proteins are selected by one or methods that include bait-versus-library screening; pairwise (gene by gene) interaction mapping; and/or prior knowledge or a hypothesis regarding a pathway or an interacting protein pair.

A F1/F2 reporter fragment pair is generated by fragmentation of a suitable reporter (examples of additional reporters are in Table 1 and in U.S. Pat. No. 6,270,964). Two expression constructs comprising the complementary fragments are made, in which the expression of a fusion protein is driven by a suitable promoter. One of the expression constructs comprises a first gene fused in frame to reporter fragment F1, and the other comprises a second gene fused in frame to reporter fragment F2. Optimally, a flexible linker, such as that described in Example 1 below, is fused between the fluorescent protein fragment and the gene of interest to facilitate fragment complementation. Therefore, each expression vector codes for a fusion protein consisting of an operably linked gene of interest, a flexible linker, and either F1 or F2 of the chosen reporter. Such compositions are a subject of the present invention. Fragments may be fused at either the 3' or 5' end of the gene of interest with the linker between the fragment and the gene of interest. Selection of the fusion orientation may be based on a prior understanding of a particular protein function or based on empirical evidence of optimal fragment orientations. As shown in FIG. 1, since either F1 or F2 can be fused to the gene of interest and the orientation of the fusion can either be 5' or 3' relative to the gene of interest, four different DNA constructs are possible for any single gene of interest.

To generate the PCA for a pair of proteins e.g. A and B, constructs encoding A and B fused to complementary reporter fragments F1 and F2, respectively, are co-transfected into cells using transfection methods suitable for the particular vector and cell type. If proteins A and B interact, fragments F1 and F2 are brought into close proximity where they are capable of folding and reconstituting an active reporter. The resulting signal can then be detected, quantified, visualized or imaged by a variety of standard methods for optical detection of the chosen reporter. All of these methods can be used in automated, high-throughput formats using instrumentation well known to those skilled in the art.

It will be apparent to one skilled in the art that the choice of expression vector depends on the cell type for assay construction, whether bacterial, yeast, mammalian, or other cell type; the desired expression level; the choice of transient versus stable transfection; and other typical molecular and cell biology considerations. A wide variety of other useful elements can be incorporated into appropriate expression vectors, including but not limited to epitope tags, antibiotic resistance elements, and peptide or polypeptide tags allowing subcellular targeting of the assays to different subcellular compartments (e.g. A Chiesa et al., Recombinant aequorin and green fluorescent protein as valuable tools in the study of cell signaling). The incorporation of a different antibiotic resistance marker into each of the two complementary constructs would allow for the generation of stable cell lines through double antibiotic selection pressure, whereas subcellular targeting elements would allow for the creation of assays for G-protein-coupled pathway events that occur within a particular subcellular compartment, such as the mitochondria, Golgi, nucleus, or other compartments.

A variety of standard or novel expression vectors can be chosen based on the cell type and desired expression level; such vectors and their characteristics will be well known to one skilled in the art and include plasmid, retroviral, and adenoviral expression systems. In addition, there is a wide range of suitable promoters including constitutive and inducible reporters that can be used in vector construction. If an inducible promoter is used, the signal generated in the assay will be dependent upon activation of an event that turns on the transcription of the genes encoded by the PCA constructs.

Reporter Fragmentation

The principles of PCA assay construction have been described in detail in the References incorporated herein. While fragmentation of proteins for PCA is generally based on rational dissection of the polypeptide chain, a number of other engineering approaches can be used that will be well known to one skilled in the art. Fragments of a suitable reporter protein can be generated by starting with a cDNA encoding a full-length reporter of interest and using PCR to amplify fragments of interest. Alternatively, random fragmentation of a reporter can be performed, e.g. using 5' exonucleases to generate libraries of fragments to search for optimal pairs (Michnick, et al. U.S. Pat. No. 6,270,964). In addition, oligonucleotides encoding fragments can simply be synthesized using standard oligonucleotide synthesis techniques.

Mutant fragments can also be generated in order to generate assays tailored to the biological application and the instrumentation to be used. For example, site-directed mutagenesis of reporters, followed by fragmentation (or alternatively, site-directed mutagenesis of previously-created fragments) can be used to obtain fragments that provide altered fluorescence properties, or superior folding or maturation rates and stabilities upon fragment complementation. Site-directed mutagenesis is achieved by any of a number of approaches that are well known to one skilled in the art (see M Ling & B H Robinson, 1997, Approaches to DNA mutagenesis: an overview. Anal Biochem 254:157-78). Selected examples of such methods are provided here; however, these examples are not intended to be limiting for the practice of this invention. Suitable methods could include combinations of random mutagenesis and directed evolution or DNA shuffling schemes (A. L. Kurtzman et al., 2001, Advances in directed protein evolution by recursive genetic recombination: applications to therapeutic proteins, Curr Opin Biotechnol 2001 August; 12(4):361-70; S W Santoro et al., 2002, Directed evolution of the site specificity of Cre recombinase. Proc Natl Acad Sci USA 2002 99:4185-90; Z. Shao et al., 1996, Engineering new functions and altering existing functions, Curr Opin Struct Biol 6:513-8; S. Harayama, 1998, Artificial evolution by DNA shuffling, Trends Biotechnol 1998, 16:76-82); assembly PCR or gene synthesis approaches (WP Stemmer et al., 1995, Single-step assembly of a gene and entire plasmid from large numbers of oligodeoxyribonucleotides, Gene 164 (1):49-53; R M Horton et al. 1993, Gene splicing by overlap extension. Methods Enzymol. 217:270-9), or fragmentation by exo- or endo-nuclease digestion (M. Kitabatake and H. Inokuchi, 1993, A simplified method for generating step-wise deletions using PCR, Gene 123:59-61; S. Henikoff, 1990, Ordered deletions for DNA sequencing and in vitro mutagenesis by polymerase extension and exonuclease III gapping of circular templates, Nucleic Acids Res 18(10):2961-6). A particularly powerful method is based on 5'-template-assisted long-range plasmid polymerization as exemplified by a number of commercial mutagenesis kits, for example the Quick-Change™ system (Stratagene). In addition, various forms of directed evolution based on DNA shuffling could also be used to generate completely novel PCAs. Although it is expedient to carry out the engineering and construction of PCAs at the DNA level and then either allow a cell to produce the fusion proteins, it is not essential. The assays described herein can be performed in vivo or in vitro. In vitro assays may facilitate characterization of a large number of GPCRs. For example, fusion proteins can be made in vitro using in vitro expression techniques that are well known to those skilled in the art such as baculovirus expression systems and alternative approaches to polypeptide expression. In addition, for in vitro PCAs, fusion polypeptides could be produced synthetically by peptide synthesis, or by ligation of peptide fragments encoding molecules of interest to create peptide fusions with the reporter fragments. Such assays could be used, for example, to characterize the binding of orphan GPCRs to peptide ligands. The GPCRs could each be tagged with a F1 fragment of a reporter and immobilized on a solid surface such as a chip. The chip could then be exposed to a library, such as a peptide library, in which each peptide is tagged with a complementary (F2) fragment of a reporter. Binding of a peptide to a GPCR would be detected by reconstitution of the reporter activity through the association of F1 and F2. The identity of the binding peptide could then be assessed, for example by any one of a variety of proteomic methods including mass spectroscopy. Such assays for screening and de-orphanization are also a subject of the present invention. The present invention is not limited to the assay format used or the detection method for the assay.

Selection of an Appropriate Reporter

The general characteristics of reporters suitable for PCA have previously been described (References incorporated herein). A preferred embodiment of the present invention involves cell-based assays generating a fluorescent or luminescent signal are particularly useful. Examples of reporters that can be used in the present invention are listed in Table 1. It will be appreciate by one skilled in the art that the choice of reporter is not limited. Rather, it will be based on the desired assay characteristics, format, cell type, spectral properties, expression, time-course and other assay specifications. For any reporter of interest various useful pairs of fragments can be created, for example using the methods taught in U.S. Pat. No. 6,270,964 and the References incorporated herein, and then engineered in order to generate fragments that produce a brighter signal or a specific color readout upon fragment reassembly. It will be obvious to one skilled in the art that various techniques of genetic engineering can be used to create useful fragments and fragment variants of any of the reporters that are the subject of this invention.

It will be appreciated by a person skilled in the art that the ability to select from among a wide variety of reporters makes the invention particularly useful for drug discovery on a large scale. In particular, reporters can be selected that emit light of a specific wavelength and intensity that may be suitable for a range of protein expression levels, cell types, and detection modes. The flexibility is an important feature of the invention because of the wide range of signaling events, or biochemical processes, linked to GPCRs. For some biochemical events, activation of a GPCR—for example, by the binding of an agonist—will lead to an increase in the association of a GPCR and a cognate binding protein, or of two elements 'downstream' in the G-protein-coupled pathway, such as a kinase and its substrate. An increase in the association of the two proteins that form the PCA pair leads to an increase in the signal generated by the reassembled reporter fragments. In that case, a high-throughput assay format can be used to measure the fluorescent signal that is proportional to the amount of the complex of interest. For quantitative assays, where the readout is an increase or decrease in signal intensity, any of the reporters discussed in the present invention can be used and each reporter has various pros and cons that are well understood by those skilled in the art of cell biology. Enzymes—for which the catalytic reaction generates a fluorescent, phosphorescent, luminescent or other optically detectable signal—may be best suited for purely quantitative assays. Upon fragment complementation, the reconstituted enzyme acts upon a substrate to generate a fluorescent or luminescent product, which accumulates while the reporter is active. Since product accumulates, a high signal-to-noise can be generated upon fragment complementation. Such assays are particularly amenable to scale-up to 384-well or 1536-well formats and beyond, and are compatible with standard and ultra high-throughput laboratory automation.

Preferred reporters for the present invention include but are not limited to a beta-lactamase PCA or a luciferase PCA such as with a firefly luciferase or *Renilla* luciferase. Each of these enzymes has been successfully used as a cell-based reporter in mammalian systems (S Baumik & S S Gambhir, 2002, Optical imaging of *renilla* luciferase reporter gene expression in living mice, Proc. Natl. Acad. Sci., USA 2002, 99(1): 377-382; Lorenz et al., 1991, Isolation and expression of a cDNA encoding *renilla reniformis* luciferase, Proc. Natl. Acad. Sci. USA 88: 4438-4442; G. Zlokarnik et al., 1998, Quantitation of transcription and clonal selection of single living cells with beta-lactamase as reporter, Science 279: 84-88). As an example of the construction of a PCA, beta-lactamase PCAs have been constructed with cell-permeable substrates that generate a high signal to background upon cleavage (A Galarneau et al., 2000, Nature Biotechnol. 20: 619-622). The beta-lactamase PCA is a sensitive and quantitative assay suitable for HTS. This PCA has been used with CCF2/AM, a green fluorescent molecule which becomes blue upon cleavage of the beta-lactam ring by beta-lactamase; the blue-green ratio is therefore a measure of the activity of beta-lactamase which is reconstituted upon protein-fragment complementation. Luciferase PCAs can also be used with cell-permeable substrates to generate HTS assays suitable for the present invention (e.g. R Paulmurugan et al., 2002, Non-invasive imaging of protein-protein interactions in living subjects by using reporter protein complementation and reconstitution strategies, Proc. Natl. Acad. Sci. USA 99: 15608-15613). With suitable modifications, any of these PCAs can also be used in vivo or in vitro for the present invention. It will be apparent to one skilled in the art that PCAs based on inherently fluorescent, phosphorescent or bioluminescent proteins can be read either in high-content formats or in high-throughput formats. These PCAs have the advantage of not requiring the addition of substrate; however, the signal generated is usually lower than that generated by an enzymatic reporter.

Calcium-sensitive photoproteins would be particularly useful as PCAs for GPCR assays. These could be based on fragments of aequorin, obelin; or any other calcium-sensitive protein (e.g. M D Ungrin et al., 1999, An automated aequorin luminescence-based functional calcium assay for G-protein-coupled receptors, Anal Biochem. 272: 34-42; Rizzuto et al., 1992, Rapid changes of mitochondrial calcium revealed by specifically targeted recombinant aequorin, Nature 358 (6384): 325-327; Campbell et al., 1988, Formation of the calcium activated photoprotein obelin from apo-obelin and mRNA in human neutrophils, Biochem J. 252 (1):143-149). Aequorin, a calcium-sensitive photoprotein derived from the jellyfish *Aequorea victoria*, is composed of an apoprotein (molecular mass ~21 kDa) and a hydrophobic prosthetic group, coelenterazine. Calcium binding to the protein causes the rupture of the covalent link between the apoprotein and the coelenterazine, releasing a single photon. The rate of this reaction depends on the calcium concentration to which the photoprotein is exposed. Intact aequorin with coelenterazine has been used to monitor calcium flux in cell-based assays for GPCRs. Obelin is a 22-kDa monomeric protein that also requires coelenterazine for signal generation. Construction of an aequorin PCA or an obelin PCA would enable assays for G-protein-coupled receptors and pathways in which photon release only occurs if the reporter fragments are associated as a result of a ligand-protein interaction or a protein-protein interaction. Such an assay would combine measures of pathway activation with calcium flux, making the assays extraordinarily sensitive for GPCR studies.

Although small monomeric reporters are preferred for this invention due to the small size of the reporter fragments, it will be apparent from the prior art that multimeric enzymes such as beta-galactosidase, beta-glucuronidase, tyrosinase, and other reporters can also be used in the present invention. A number of multimeric enzymes suitable for PCA have previously been described (U.S. Pat. No. 6,270,964). Fragments of multimeric proteins can be engineered using the principles of PCA described in the prior art; alternatively, naturally-occurring fragments or engineered low-affinity subunits of multimeric enzymes can be used including the widely-used beta-galactosidase alpha and omega complementation systems (see References). The naturally-occurring fragments of beta-galactosidase and protocols for their use have been developed and distributed by DiscoveRx, Inc. (Fremont, Calif.) and by distributors including Stratagene (Q-Tag detection kit,) and can be used in conjunction with any of the fragment complementation assays and GPCR signaling proteins taught in the present invention. The engineered low-affinity subunits of beta-gal are sold by Applied Biosystems, Inc. Substrates suitable for the generation of fluorescent and luminescent signals upon beta-gal complementation are also widely available (see for example Promega Corp. for Beta-Glo protocols and reagents) and can be used in conjunction with the present invention.

For some G-protein-coupled events, activation of the pathway leads to the translocation of a pre-existing protein-protein complex from one sub-cellular compartment to another, without an increase in the total number of protein-protein complexes. In that case, the fluorescent signal generated by the reassembled reporter at the site of complex formation within the cell can be imaged, allowing the trafficking of the complex to be monitored. Such "high-content" PCAs can be engineered for any suitable reporter for which the signal remains at the site of the protein-protein complex. Examples include the DHFR PCA, which has been used for high-content assays of signal transduction pathways (I Remy & S Michnick, 2001, Visualization of Biochemical Networks in Living Cells, Proc Natl Acad Sci USA, 98: 7678-7683) and also for high-throughput assays (I Remy et al., 1999, Erythropoietin receptor activation by a ligand-induced conformation change, Science 283: 990-993). Reconstituted DHFR binds methotrexate (MTX); if the MTX is conjugated to a fluorophore such as fluorescein, Texas Red, or BODIPY, the PCA signal can be localized within cells. Additional reporters particularly useful for high-content assays are described in U.S. Pat. No. 6,270,964 and include the green fluorescent protein (GFP) from *Aequorea victoria*.

PCAs based on GFP, YFP, and other inherently fluorescent, luminescent or phosphorescent protein reporters are preferred embodiments of the present invention. Any number of fluorescent proteins have been described in the scientific literature (e.g. RY Tsien, 1998, The Green Fluorescent Protein, in: Annual Reviews of Biochemistry 67: 509-544; J Zhang et al., 2000, Creating new fluorescent probes for cell biology, Nature Reviews 3: 906-918). Any mutant fluorescent protein can be engineered into fragments for use in the present invention. Suitable reporters include YFP, CFP, dsRed, mRFP, 'citrine', BFP, PA-GFP, 'Venus', SEYFP and other AFPs; and the red and orange-red fluorescent proteins from Anemonia and Anthozoa.

Reporters generating a high signal in a cellular background are preferred for the present invention. For example, PCAs based on YFP, SEYFP, or 'Venus' (T Nagai et al., 2002, A variant of yellow fluorescent protein with fast and efficient maturation for cell-biological applications, Nature Biotech. 20: 87-90) are particularly suitable for the present invention. PCAs based on proteins for which the signal can be triggered, such as a kindling fluorescent protein (KFP1) (D M Chudakov et al., 2003, Kindling fluorescent proteins for precise in vivo photolabeling, Nat. Biotechnol. 21, 191-194), a photoconverting fluorescent protein such as Kaede (R Ando et al., 2002, An optical marker based on the uv-induced green-red photoconversion of a fluorescent protein, Proc. Natl. Acad. Sci. USA, 2002, 99 (20): 12651-12656), or a photoactivatable protein such as PA-GFP (G H Patterson et al., 2002, A photoactivatable GFP for selective labeling of proteins and cells, Science 297: 1873-1877) may have advantages, particularly in cases where it is necessary to capture very rapid signaling events. KFP1 is derived from a unique GFP-like chromoprotein asCP from the sea anemone Anemonia sulcata. asCP is initially nonfluorescent, but in response to intense green light irradiation it becomes brightly fluorescent (kindles) with emission at 595 nm. Kindled asCP relaxes back to the initial nonfluorescent state with a half-life of <10 seconds. Alternatively, fluorescence can be "quenched" instantly and completely by a brief irradiation with blue light. The mutant (asCP A148G, or KFP1) is capable of unique irreversible photoconversion from the nonfluorescent to a stable bright-red fluorescent form that has 30 times greater fluorescent intensity than the unkindled protein, making it particularly suitable for live cell PCAs.

It will be apparent to one skilled in the art that any of these reporters can be used to construct assays based on the principles and methods described herein by simply generating fragment pairs for the reporter that is to be used; substituting the fragment pairs for the desired reporter in the fusion constructs; expressing them at a level suitable for detection of the signal of interest; and performing the assay under conditions suitable for the detection of the signal that is generated upon fragment complementation for that particular reporter. Such assay conditions can be found in the biochemical literature and are well known to those skilled in the art.

Instrumentation

The high-throughput assays described above generate optically detectable signals that can be read on commercially available instrumentation, including fluorescence plate readers, luminometers, and flow cytometers. Such instrumentation is widely available from commercial manufacturers, including Molecular Devices, Packard, Perkin Elmer, Becton Dickinson, Beckman Coulter, and others. All such assays can be constructed in multiwell (96-well and 384-well) formats. The high-content assays described above generate optically detectable signals that can be spatially resolved within sub-cellular compartments. The resulting images can be captured with automated microscopes, confocal imaging systems, and similar devices. Suitable imaging instrumentation is widely available from a variety of commercial manufacturers including Molecular Devices (Universal Imaging), Amersham Bioscience, Cellomics, Evotec, Zeiss, Q3DM, Atto, and others. Image analysis software such as MetaMorph, the publicly available IMAGE software from the National Institutes of Health (http://rsb.info.nih.gov/nih-image/) and various proprietary software packages are used to distinguish the signal emanating from different subcellular compartments (membrane, cytosol, nucleus) and to quantitate the total fluorescence per cell. In addition, multi-well PCA formats for the present invention can be constructed for array-based assay formats, including reverse transfection methods such as those provided by Akceli Inc., allowing the rapid, simultaneous processing of a large number of different PCAs on a single array.

Selection of G-Protein-Coupled Pathway Elements for Assay Construction

The present invention can be used to construct assays for G-protein-coupled receptors themselves, for example by tagging the intracellular (C-terminal) portion of the GPCR with a reporter fragment and assaying its self interactions, receptor interactions with ligands, with other receptors, with kinases or phosphatases, with receptor activated modulator proteins, or with other intracellular proteins. For example, the various interactions among GPCRs and G-proteins can be assayed using the methods provided herein. The advantage is the ability to understand the intracellular machinery linked to a particular GPCR and to construct an assay for any step in a pathway. The advantages of being able to construct screening assays for various steps in a G-protein-coupled pathway, starting with the receptor and moving down the entire signaling cascade, include the ability to screen for compounds that may act at any one of various potentially druggable targets in a G-protein-coupled pathway and to de-orphanize receptors by identifying the signaling machinery to which the receptor is linked.

Suitable pairs of interacting molecules for assay construction can be identified by any one of the methods outlined in FIG. 1. PCA enables a systematic characterization of the interactions made among the GPCRs in living cells by first examining whether different pairs of GPCRs generate a PCA signal in a cell type of interest and then determining whether the signal amount or subcellular location is affected by agents that modify cell signaling. In this way, the functional interactions among the hundreds of GPCRs can be 'mapped' using PCA. For example, a GPCR tagged with one complementary fragment of a reporter can be used as 'bait' to screen a cDNA library tagged with a second complementary fragment of a reporter (bait-vs.-library screening). In this respect PCA is an alternative to the widely-used yeast-two-hybrid system for the identification of interactions among G-protein-coupled signaling components. Systematic screening can also be performed to identify pathway elements; for example, novel or orphan GPCRs tagged with F1 of a suitable reporter can be tested individually against other proteins tagged with complementary fragment F2 (gene-by-gene analysis). The presence of a PCA signal indicates an interaction between the two proteins tagged with the complementary fragments. For example, the cognate G-proteins linked to particular GPCRs can be identified or the kinases linked to specific GPCRs can be identified by testing each protein against the other in a PCA. The presence of a PCA signal indicates an interaction between the two assay components. The advantage of the present invention is that, once an interaction has been identified, an assay is in hand that can be used to screen for pathway modulation, to de-orphanize receptors, or to screen for compounds that modulate the pathway of interest by using a high-content or high-throughput PCA as a screen.

The components of G-protein-coupled pathways have been partially elucidated, and the known or hypothesized interactions can readily be used to design assays according to the present invention. The present invention encompasses assays for a variety of steps in G-protein-coupled pathways. A number of these steps are described in detail below based on the biochemical literature, and are listed in Table 2. Any of the protein-protein interactions reported to date can be used as the basis for the construction of protein-fragment complementation assays or enzyme-fragment complementation assays. Such assays can include the GPCRs themselves; G-proteins (alpha, beta and gamma subunits); adenylyl cyclase (R and C subunits); protein kinases (including but not limited to GRK, PCA, PKC, MAPK, ERK, and others); protein phosphatases (PPP2A and others); phospholipases, such as phospholipase C (PLC); receptor-activity-modifying proteins (RAMPs); lipid transferases (farnesyl transferase, myristoyl transferase, palmitoyl transferase); ion exchange regulatory factors; GIRKs; beta-arrestins; E3 ligases; Ubiquitin monomer or polypeptide; RDG proteins; phosphodiesterases such as PDE4; cytokine and growth factor receptors that exhibit cross-talk with GPCRs; and transcription factors such as ELK, CREB and CBP.

All of the assays that are the subject of the present invention are of general use as validation assays or in basic experimental biology research as well as in drug discovery. For example, these assays can be used in conjunction with RNA interference methods to link specific genes to G-protein-coupled pathways. This can be accomplished by introducing, for example, a small interfering RNA (siRNA) into a cell-based fragment complementation assay and determining whether the siRNA reduces the signal generated by the interacting protein pair. Any number of other cellular probes can be used in a similar manner, including dominant negative genes, drugs, peptides, antibodies and other biochemical or biological reagents. In addition to functional annotation, target validation and pathway mapping, the assays described herein are all amenable to high-throughput screening and drug discovery.

TABLE 2

Interacting elements of G-protein-coupled pathways suitable for the construction of fragment complementation assays

| First protein | Second protein | Reported event | Reference |
| --- | --- | --- | --- |
| GPCR | GPCR | receptor homo- or hetero-dimerization | S. Angers et al., 2002, Dimerization: an emerging concept for GPCR ontogeny and function, Annu. Rev. Pharmacol. Toxicol. 42: 409-435. |
| GPCR | ligand (either a peptide or a small-molecule ligand could be used in PCA) | ligand binding to receptor | U Gether, 2000, Uncovering molecular mechanisms involved in activation of G Protein-Coupled Receptors, in: Endocrine Reviews 21: 90-113. |
| GPCR | G-protein subunit | Gα, Gβ, or Gγ binding to intracellular portion of G-protein coupled receptor; specificity varies based on receptor, ligand, and cognate Gα homologue | NA Sarvazyan et al., 2002, Fluorescence Analysis of Receptor-G protein Interactions in Cell membranes, Biochemistry 41: 12858-12867; E Hermans, 2003, Biochemical and Pharmacological control of the multiplicity of coupling at GPCRs, Pharmacology & Therapeutics 99:25-44. |

TABLE 2-continued

Interacting elements of G-protein-coupled pathways suitable for the construction of fragment complementation assays

| First protein | Second protein | Reported event | Reference |
|---|---|---|---|
| GPCR | beta-arrestin | b-arrestin binds to agonist-occupied receptor | LM Luttrell & RJ Lefkowitz, 2002, The role of beta-arrestins in the termination and transduction of G-protein-coupled receptor signals, J. Cell. Sci. 115: 455-465. |
| GPCR | GRKs (GPCR kinases); multiple homologues | binding and phosphorylation of GPCR by GRK promotes binding of beta-arrestin to GPCRs | AE Brady & LE Limbird, 2002, G-protein-coupled receptor interacting proteins: emerging roles in localization and signal transduction, Cell Signal 14: 297-309 |
| GPCR | PKA, PKC, Src, Casein kinases; Raf, MEK, ERK | phosphorylation of the beta-2 adrenoreceptor by the cyclic AMP-dependent protein kinase, PKA, switches its coupling from Gs to Gi and induces receptor internalization; binding of c-Src tyrosine kinase to GPCR mediates Src-dependent phosphorylation of GRK | Daaka et al., 1997, Switching of the coupling of the beta-2-adrenergic receptor to different G-proteins by protein kinase A, Nature 390: 88-91; G Fan et al., 2001, C-src tyrosine kinase binds the beta-2-adrenergic receptor via phospho-Tyr-350, phosphorylates GRK2 and mediates agonist-induced receptor desensitization, J. Biol. Chem. 276: 13240-13247; N Yuan et al., 1994, cAMP-dependent protein kinase A and protein kinase C consensus site mutations of the beta-adrenergic receptor, J. Biol. Chem. 269: 23032-23038; R Winstel 1996, Protein kinase cross-talk: membrane targeting of the beta-adrenergic receptor kinase by protein kinase C, Proc. Natl. Acad. Sci. USA 93: 2105-2109. |
| GPCR | E3 ligase; Ubiquitin | ubiquitination of GPCR by an E3 ligase targets the receptor for downregulation | A. Ciechanover, 1998, The ubiquitin-proteasome pathway: on protein death and cell life, The EMBO Journal 17: 7151-7160. |
| GPCR | Protein phosphatase (PP2A and homologues) | dephosphorylation of phosphorylated GPCR | JA Pitcher, 1995, The G-protein coupled receptor phosphatase: a protein phosphatase type 2A with a distinct subcellular distribution and substrate specificity, Proc. Natl. Acad. Sci. USA 92: 8343-8347 |
| GPCR | RAMPs (receptor-activity-modulating proteins); several homologues | RAMPs are single-transmembrane proteins that transport receptors to the cell surface | JA Fischer et al., 2002, Functional relevance of G-protein-coupled-receptor-associated proteins exemplified by receptor-activity-modifying-proteins (RAMPS), Biochem. Soc. Trans. 30(4): 455-460. |
| GPCR | PDZ-containing, EVH-containing and Homer family proteins | binding of C-terminal GPCR sequences and regulation of receptor function; some GPCRs interact directly, via their C-terminal domain, with proteins containing PDZ and Enabled/VASP homology (EVH)-like domains. | Xiang, 2002, The PDZ-binding motif of the β2-adrenergic receptor modulates receptor trafficking and signaling in cardiac myocytes, J. Biol. Chem. 277: 33783-33790; RA Hall, 1999, Heptahelical receptor signaling: beyond the G protein paradigm, J. Cell Biol. 145: 927-932. |
| GPCR | growth factor or cytokine receptors (EGFR, PDGFR, VEGFR, HGH receptor, GM-CSF receptor, IL receptors, etc.) | cross-talk between receptors | ML Grimes & HM Miettinen, 2003, Receptor tyrosine kinase and G-protein coupled receptor signaling and sorting within endosomes, j. Neurochem. 84: 905-918. |
| GPCR | Na+/H+ exchanger regulatory factors; GIRKs (G-protein activated inwardly rectifying K+ channels) | exchange protein interactions that control cell signaling linked to certain GPCRs; certain GPCRs including the alpha-2a-adrenergic receptor couple to GIRKs | RA Hall, 1998, The beta-2 adrenergic receptor interacts with the Na+/H+ exchanger regulatory factor to control Na+/H+ exchange, Nature 392: 626-630; MJ Mahon et al., 2002, Na+/H═ exchanger regulatory factor 2 directs parathyroid hormone 1 receptor signaling, Nature 417: 858-861. |
| G-protein subunit Gα, Gβ, or Gγ | G-protein subunit Gβ, Gβ, or Gγ; AGS proteins (Activators of G Proteins) | Association or dissociation of Gα/Gβ. Gβ/Gγ, Gα/Gγ | J-Z. Yu & MM Rasenick, 2002, Real-time visualization of a fluorescent Gαs: dissociation of the activated G-protein from the plasma membrane, Mol. Pharmacol. 61: 352-359; NA Sarvazyan et al., 2002, Fluorescence Analysis of Receptor-G protein Interactions in Cell membranes, Biochemistry 41: 12858-12867. |
| G-protein subunit Gα, Gβ, or Gγ | Adenylyl Cyclase | G-proteins coupled through adenylyl cyclase to generate the second messenger cAMP | RK Sunahara et al., 1996, Complexity and Diversity of mammalian adenylyl cyclases, Annu. Rev. Pharmacol. Toxicol. 36: 461-480. |
| G-protein subunit Gα, Gβ, or Gγ | Phospholipase C | GPCRS that couple to Gq family members stimulate PLC resulting in release of 1P3 and diacylglycerol | JL Blank et al., 1992, Activation of cytosolic phosphoinositide phospholipase C by G-protein β/γ subunits, J. Biol. Chem. 267: 23069-23075; M Schmidt et al., 2000, G Protein-coupled receptor-induced sensitization of phospholipase C stimulation by receptor tyrosine kinases, J. Biol. chem. 275: 32603-32610. |
| Beta-arrestins | GPCR | beta-arrestins as desensitizers for GPCRs | RH Oakley et al., 2000, differential affinities of visual arrestin, beta-arrestin1, and beta-Arrestin2 for G Protein-coupled receptors delineate two major classes of receptors, J. Biol. chem. 275: 17201-17210. |

TABLE 2-continued

Interacting elements of G-protein-coupled pathways suitable for the construction of fragment complementation assays

| First protein | Second protein | Reported event | Reference |
| --- | --- | --- | --- |
| Beta-arrestins | GPCRs; Src kinase; Shc; MAPK; JNK3; ASK; MKK4; Raf; MEK; ERK1/2; AKT | beta-arrestins as scaffolds for intracellular protein kinase cascades | LM Luttrell & RJ Lefkowitz, 2002, The role of beta-arrestins in the termination and transduction of G-protein-coupled receptor signals, J. Cell. Sci. 115: 455-465. |
| G-protein subunit Gα, Gβ, or Gγ | GPCRs; GRK; Src kinase; Shc; MAPK; JNK3; ASK; MKK4; Raf; MEK; ERK1/2; AKT | G-protein-modulated kinase signaling cascades (ras/raf, MAPK, JNK, AKT, ERK/ELK and other signaling cascades) | EM Hur & KT Kim, 2002, G-protein-coupled receptor signalling and cross-talk : achieving rapidity and specificity, Cell. Signaling 14: 397-405. |
| Beta-arrestins | clathrin; NSF; AP2; Arf-6 | Beta-arrestin promotes internalization of receptors via clathrin-coated vesicles; interacts with clathrin, adaptor protein AP-2, N-ethylmaleimide-sensitive fusion protein (NSF) and Arf 6 | LM Luttrell & RJ Lefkowitz, 2002, The role of beta-arrestins in the termination and transduction of G-protein-coupled receptor signals, J. Cell. Sci. 115: 455-465. |
| Beta-arrestins | Ubiquitin; MDM2 | beta-arrestins as substrates for ubiquitination by E3 ligases; in particular, MDM2 binds to and ubiquitinates beta-arrestin | SK Shenoy et al., 2001, Regulation of receptor fate by ubiquitination of activated β-2-adrenergic receptor and beta-arrestin, Science 294: 1307-1313. |
| Beta-arrestins | dishevelled (DSH) | beta-arrestin1 interacts with DSH in a phosphorylation-dependent manner | W Chen et al., 2001, beta-arrestin1 modulates lymphoid enhancer factor transcriptional activity through interaction with phosphorylated dishevelled proteins, Proc. Natl. Acad. Sci. USA 98: 14889-14894 |
| Beta-arrestins | PDE4 | beta-arrestins recruit the cAMP-degrading PDE4 phosphodiesterases to the β2adrenergic receptor | GS Baillie et al., 2003, beta-arrestin-mediated PDE4 cAMP phosphodiesterase recruitment regulates β-adrenoceptor switching from Gs to Gi, Proc. Natl. Acad. Sci. USA 100(3): 940-945 |
| RGS (regulators of G-protein signaling) | Gα; GPCR | RGS as desensitizer of signaling components; bind directly to Gα | SP Heximer et al., 2001, Mechanisms governing subcellular location and function of human RGS2, J. Biol. Chem. 276: 14195-14203; RJ Kimple et al., 2003, Established and emerging fluorescence-based assays for G-Protein Function, in: Combinatorial Chemistry & High-Throughput Screening, 6: 1-9. |
| GRKs | tubulin, ribosomal protein P2, synucleins, phosducins; c-src | GRK-mediated phosphorylation of intracellular substrates synucleins, phosducins, ribosomal proteins, tubulins; c-src phosphorylates GRK2 on tyrosine residues, triggering GRK2 degradation | JLR Freeman, 2002, Adrenergic receptor-stimulated, GRK2-mediated phos-phorylation of ribosomal protein P2, Biochemistry 41: 12850-12857; S Sarmago, 1999, Agonist-dependent phosphorylation of the G-protein-coupled receptor kinase 2 (GRK2) by Src tyrosine kinase, J. Biol. Chem. 274: 34411-34416 |
| Farnesyl transferase(s), palmitoyl transferase(s), myristoyl transferase(s) | GRKs, GPCRs, Gα | Membrane targeting of GRKs GPCRs, and Gα by farnesylation, palmitoylation, and/or myristoylation | Y Okamoto, 1997, Palmitoylation of human endothelin B, J. Biol. Chem. 272: 21589-21596; BF O'Dowd, 1989, Palmitoylation of the human beta-2 adrenergic receptor, J. Biol. Chem. 264: 7564-7569; P Svoboda and J Novotny, 2002, Hormone-induced subcellular redistribution of trimeric G proteins, Cell. Mol. Life Sci. 59: 501-512 |
| Phospholipase(s) C (PLC) | Gαq, Gαi, Gβ, Gγ, GPCR, RTK | GPCRs activate PLC via G-proteins; GPCRs sensitize PLC stimulation by RTKs; Gβγ activates phospholipase C | M Schmidt et al., 2000, G Protein Coupled Receptor-induced sensitization of phospholipase C stimulation by Receptor Tyrosine Kinases; J. Biol. Chem. 275: 32603-32610; JH Exton, 1996, Regulation of phosphoinositide phospholipases by hormones, neurotransmitters, and other agonists linked to G-proteins, Annu. Rev. Pharmacol. Toxicol. 36: 481-509 |
| PKA (cyclic AMP-dependent protein kinase) | PKA (RI/RII), PKA (C) GSK3, GPCRs, AKAPs, PKC | PKA regulatory subunits (R) interact and regulate catalytic subunits (C) in response to cAMP, PKA phosphorylates GPCRs and GSK3; A-kinase anchoring proteins (AKAPs) interact with PKA; AKAPs can recruit both PKA and PKC to specific subcellular locations via interactions with the various isoforms of each family of kinases. Each of these proteins has numerous homologues. | X Fang et al., 2002, Convergence of multiple signaling cascades at glycogen synthase kinase 3, Mol. Cell. Biol. 22: 2099-2110; ML Ruehr et al., 1999, Cyclic AMP-dependent protein kinase binding to A-kinase anchoring proteins in living cells by fluorescence resonance energy transfer of green fluorescent protein fusion proteins, J. Biol. Chem. 274: 33092-33096 SR Adams et al., 1991, fluorescence ratio imaging of cyclic AMP in single living cells, Nature 349: 694-697; GA Perkins et al., 2001, PKA, PKC, and AKAP localization in and around the neuromuscular junction, Neuroscience 2: 17.<br>Also see review articles in References listed herein. |

TABLE 2-continued

Interacting elements of G-protein-coupled pathways suitable for the construction of fragment complementation assays

| First protein | Second protein | Reported event | Reference |
| --- | --- | --- | --- |
| Transcription factors e.g. ELK, CREB, CBP, NFkB | penultimate components of signaling of GPCRs via second messengers (calcium, cAMP, IP3) and via kinase cascades (ERK/ELK) | GPCR-dependent activation of cAMP-responsive element binding protein (CREB) via PKA-dependent phosphorylation; | JC Chrivia et al., 1993, Phosphorylated CREB binds specifically to the nuclear protein CBP, Nature 365: 855-859 |

In order to exemplify these principles, we used various known pairs of interacting proteins to construct assays for GPCRs and G-protein-coupled pathways, including receptor/receptor assays, receptor/G-protein assays, and receptor/beta-arrestin assays. For the latter, we demonstrated both quantitative, agonist-dependent association of proteins as well as high-content, kinetic assays in living cells.

EXAMPLE 1

Dimerization of GPCRs

A growing number of studies have shown that GPCRs are capable of forming homodimers or heterodimers (S. Angers et al., 2002, Dimerization: an emerging concept for GPCR ontogeny and function, Annu. Rev. Pharmacol. Toxicol. 42: 409-435; M K Dean et al., 2001, Dimerization of G-protein-coupled receptors, J. Med. Chem. 44: 4594-4614). Receptor self-association and subsequent changes in receptor activity have been reported for the beta2-adrenergic receptor (T. E. Hebert, 1996, A peptide derived from a beta2-adrenergic receptor transmembrane domain inhibits both receptor dimerization and activation, J. Biol. Chem. 271: 16384-16392), in addition to the delta-opioid receptors, the dopamine receptors, and other GPCRs. It has been shown that agonists can stabilize the dimeric forms of different GPCRs (U. Gether et al., 2000, Uncovering molecular mechanisms involved in activation of G-protein-coupled receptors, Endocrine Reviews 21:90-113), suggesting that homodimerization may play a role directly in receptor activation or, alternatively, in the subsequent agonist-dependent desensitization and internalization process (He et al., 2002, Regulation of opioid receptor trafficking and morphine tolerance by receptor oligomerization, Cell 108: 271-282). In addition to homo-dimerization, evidence has accumulated demonstrating the possible importance of hetero-dimerization between closely related receptor subtypes, which may also be critical for targeting functional receptors to the cell surface and for drug tolerance. Standard biochemical methods have been used to study receptor dimerization, including co-immunoprecipitation and gel shift assays. In addition, FRET or BRET have been used to monitor homo-oligomerization and hetero-oligomerization of GPCRs (McVey et al., 2001, Monitoring receptor oligomerization using fluorescence resonance energy transfer and bioluminescence resonance energy transfer, J. Biol. Chem. 276: 14092-14099). However, the prior art is silent on the use of fragment-complementation assays to study GPCR dimerization.

A high-content assay suitable for live cells would enable monitoring of trafficking of receptor complexes between the cell membrane, endocytic vesicles, cytoplasm and other subcellular compartments in response to agonists and antagonists. We postulated that fragment complementation could be used to construct fluorescence assays for the detection of receptor-receptor dimers. Accordingly, in Example 1 we constructed a high-content, fluorescence PCA to measure the $\beta_2$-adrenergic receptor. An enhanced YFP was selected as the reporter. To generate fusion constructs for $\beta_2$AR, the full coding sequence of the cDNA for the $\beta_2$AR was amplified by PCR from a sequence-verified full-length cDNA. The resulting PCR products were cleaned up by vacuum filtration (MultiScreen PCR, Amicon) and digested with appropriate restriction enzymes to allow directional cloning. The PCR products were fused in-frame to the 5' end of either YFP[1] (SEQ ID No. 1) or YFP[2] (SEQ ID No. 3) to generate the following constructs in a pcDNA3.1 (Invitrogen) backbone: β2AR-YFP[1] and β2AR-YFP[2]. Fragments YFP[1] (SEQ ID No. 1) and YFP[2] (SEQ ID No. 3) had the following nucleotide sequences:

```
>YFP + [1] (SEQ ID No.1)
atggtgagcaagggcgaggagctgttcaccggggtggtgcccatcctggtcgagctggacggcgacgtaaacggcca caagttcagcgtgtccggcgagggcgagggcgatgccacctacggcaagctgaccctgaagttcatctgcaccaccg gcaagctgcccgtgccctggcccaccctcgtgaccaccttcggctacggcctgcagtgcttcgcccgctaccccgac cacatgaagcagcacgacttcttcaagtccgccatgcccgaaggctacgtccaggagcgcaccatcttcttcaagga cgacggcaactacaagacccgcgccgaggtgaagttcgagggcgacaccctggtgaaccgcatcgagctgaagggca tcgacttcaaggaggacggcaacatcctggggcacaagctggagtacaactacaacagccacaacgtctatatcatg gccgacaagcagtaa YFP fragment 1 translation: (SEQ ID No.2)
```

-continued
```
MVSKGEELFTGVVPILVELDGDVNGHKFSVSGEGEGDA

TYGKLTLKFICTTGKLPVPWPTLVTTFGYGLQCFARYPDHMKQHDFFKSA

MPEGYVQERTIFFKDDGNYKTRAEVKFEGDTLVNRIELKGIDFKEDGNIL

GHKLEYNYNSHNVYIMADKQ

>YFP[2] ] (SEQ ID No.3)
aagaacggcatcaaggtgaacttcaagatccgccacaacatcgaggacggcagcgtgcagctcgccgaccactacca gcagaacaccccatcggcgacggccccgtgctgctgcccgacaaccactacctgagctaccagtccgccctgagca aagacccaacgagaagcgcgatcacatggtcctgctggagttcgtgaccgccgcgggatcactctcggcatggac gagctgtacaagtaa YFP fragment 2 translation: (SEQ ID No.4)
KNGIKVNFKIRHNIEDGSVQLADHYQQNTPIGDPVLLPDNHYLSYQSAL

SKDPNEKRDHMVLLEFVTAAGITLGMDELYK
```

YFP[1] corresponded to amino acids 1 to 158 and YFP[2] (SEQ ID No. 2) to amino acids 159 to 239 of EYFP. The above sequences are the subject of U.S. patent application Ser. No. 10/724,178 filed Dec. 1, 2004 (published as U.S. 2004/0137528 on Jul. 15, 2004) and U.S. patent application Ser. No. 10/772,021 filed Feb. 5, 2004 (published as 2004/0161787 on Aug. 19, 2004). The above two applications are owned by the same assignee of the present application and electronic format sequences were submitted with the above-identified applications. All fusions were through a flexible linker encoding a 10-amino acid peptide (Gly.Gly.Gly.Gly.Ser)2. The use of a flexible linker between the gene of interest and the reporter fragment assures that the orientation and arrangement of the fusions is optimal to bring the protein fragments into close proximity (J. N. Pelletier, F.-X. C.-Valois & S. W. Michnick, 1998, Proc Natl Acad Sci USA 95: 12141-12146). DNAs from recombinant constructs were isolated on a Beckman FX robotic workstation (Beckman Coulter, Fullerton, Calif.) using Qiagen Turbo BioRobot Prep kits or manually using Qiagen Midi Prep kits. Isolated DNAs were quantitated and then normalized to a concentration of 50 ng/µl. β2AR-YFP1 and β2AR-YFP2 fusion genes were transiently expressed for 48 hours in HEK293E cells. For transient expression of the fusion constructs, HEK293E cells were plated (9,000 cells per well) in 96-well plates coated with poly-lysine and 24 hours later were co-transfected with 30 ng of DNA using Fugene transfection reagent (Roche Diagnostics, Indianapolis, Ind.) according to the manufacturer's recommendations. Following 48 hrs of expression, cells were washed once with PBS and acquired using a 40× objective on a Nikon TE-2000 equipped with a CoolSnap HQ CCD camera (excitation: 460-500 nm; emission:505-560 nm; dichroic mirror:505LP). As shown in FIG. 2 the receptors self-associated in human cells and generated an intense fluorescence signal at the cell membrane, demonstrating localization of the receptor-receptor complexes at the membrane in actively growing cells.

EXAMPLE 2

Associations of GPCRs with Subunits of Guanine Nucleotide Binding Proteins (G-Proteins)

GPCRs are coupled to their second messenger systems by heterotrimeric guanine nucleotide-binding proteins (G-proteins) comprised of subunits Galpha, Gbeta and Ggamma (C C Malbon & A J Morris, 1999, Physiological regulation of G protein-linked signaling, Physiol. Rev. 79: 1373-1430; T Gudermann et al., 1996, Diversity and selectivity of receptor-G-protein interaction, Annu. Rev. Pharmacol. Toxicol. 36: 429-459). When an extracellular ligand or agonist binds to a GPCR, the receptor exerts guanine nucleotide exchange factor activity, promoting the replacement of bound guanosine diphosphate (GDP) for guanosine triphosphate (GTP) on the Ggammasubunit. Upon binding GTP, conformational changes within the three flexible 'switch' regions of Galphaallow the release of Gbeta-gammaand the subsequent engagement of downstream effectors that are specific to each Galphasubtype. The intrinsic GTPase activity of Galpha returns the protein to the GDP-bound state. Reassociation of Gbeta-gammawith Galpha obscures critical effector contact sites, thereby terminating all effector interactions. Accordingly, the duration of G-protein-coupled signaling is determined by the lifetime of the Galpha subunit in its GTP-bound state. G-proteins have been classified into four protein families based on alpha-subunit composition: Gs, Gi, Gq and G12/13. The major effectors regulated by Galphainclude adenylyl cyclase (Gs is stimulatory and Gi is inhibitory), phopholipase C (Gq is stimulatory) and K+ channels (Gi is stimulatory). Free Gβγ can also engage specific effector systems including phospholipase C. These events could be studied by simple fluorescence assays in living cells, which would allow investigation of the associations between GPCRs and their cognate G-proteins, and between G-proteins and downstream effectors in G-protein-coupled pathways.

To generate PCA expression constructs for Gαi and Gβ1, the full coding sequences of each gene were amplified by PCR from the corresponding sequence-verified full-length cDNAs using methods described in Example 1. The following constructs were prepared: Gαi-YFP[1] and YFP[1]-Gβ1. Each of these constructs was used to construct a transient PCA to assess the association of the G-protein with the β2-adrenergic receptor. The β2AR-YFP[2] construct prepared as in Example 1 was co-transfected with Gαi-YFP[1] and transiently expressed for 48 hours in U-2 OS (human osteosarcoma) cells (FIG. 3*a*) or HEK293E (human embryonic kidney) cells (FIG. 3*b*). Images of the reconstituted fluorescent signal in live cells were acquired as described in Example 1. In a separate experiment, YFP[1]-Gβ1 was co-transfected with the β2AR-YFP2 in HEK 293E cells as described in Example 1 (FIG. 4). The results showed a bright fluorescent signal in living cells, demonstrating that the GPCR associates with both the alpha and beta subunits of the G-protein and that the resulting protein-protein complex is localized at the plasma membrane, as expected from the known biochemistry of these proteins. These assays can now be constructed for any GPCR using its cognate G-protein as a complementation partner in the PCA. Such assays can be used to monitor the association, dissociation and subcellular redistribution of receptor/G-protein complexes in response to agonists and antagonists; to screen for novel compounds that increase or decrease coupling of GPCRs to G-proteins; and to de-orphanize receptors, by identifying natural compounds that induce G-protein coupling to orphan receptors and identifying the specific Ga subtype that couples to the orphan receptor.

EXAMPLE 3

Intracellular Events Involving Beta-Arrestin

Beta-arrestins are adapter proteins that form complexes with most GPCRs and play a central role in receptor desensitization, sequestration and downregulation (for a review see Luttrell and Lefkowitz, J. Cell Science 115 (3): 455-465, 2002). Beta-arrestin binding to GPCRs both uncouples receptors from their cognate G-proteins and targets the receptors to clathrin-coated pits for endocytosis. Beta-arrestins may also function as GPCR signal transducers. They can form complexes with other signaling proteins, including Src framily tyrosine kinases and components of the ERK1/2 and JNK3 MAP kinase cascades. Beta-arrestin/Src complexes have been proposed to modulate receptor endocytosis and to act as as scaffolds for several kinase cascades. Beta-arrestin movement from the plasma membrane to intracellular vesicles has been visualized by tagging beta-arrestin with GFP and monitoring the subcellular distribution of the fluorescence in living cells (L S Barak et al., 2001, A beta-arrestin/green fluorescent protein biosensor for detecting G-protein-coupled receptor activation. J. Biol. Chem. 272: 27497-27500).

Beta-arrestin is phosphorylated on Ser412 by an unidentified protein kinase. Upon translocation to the membrane, Beta-arrestin-1 is rapidly dephosphorylated by an unidentified protein phosphatase. Fragment complementation assays can be used to identify the kinase and phosphatase that act upon beta-arrestin. For example, beta-arrestin conjugated to a first fragment of a reporter could be tested against a large number of ser/thr kinases, each conjugated to a second fragment of a reporter. These fusion constructs could then be co-transfected into cells to identify whether complexes form. If an interaction occurs, the effects of GPCR agonists and antagonists could be tested to determine if receptor activation increases or decreases the binding of a kinase to beta-arrestin. Alternatively, siRNAs for specific protein kinases could be used for gene silencing in cell-based fragment complementation assays. In this way it can be determined if silencing of a specific protein kinase diminishes or enhances the binding of beta-arrestin to other elements of the G-protein-coupled pathway. Once a kinase is linked to beta-arrestin, the b-arrestin/kinase assay can be used in high-throughput screening to identify compounds that block the pathway at that step. All of these approaches are made possible by the fragment complementation assays that are the subject of the present invention.

Ubiquitination is a biochemical process that targets proteins for degradation in the proteasome. Beta-arrestin ubiquitination is apparently required for internalization of GPCRs. Beta-arrestin-2 is ubiquitinated by an E3 ubiquitin ligase Mdm2, which has been shown to bind directly to beta-arrestin. GPCRs are also ubiquitinated by an as-yet-unidentified ubiquitin ligase. The construction of PCAs either for assays of beta-arrestin/Mdm2 or for assays of beta-arrestin/ubiquitin; for GPCR/ubiquitin; or for a GPCR/E3 ligase would allow characterization, quantitation and monitoring of the cellular events controlling receptor desensitization. As an example, we demonstrate an assay for beta-arrestin/ubiquitin.

Many GPCRs activate MAP kinases, leading to the activation of protein kinase ERK 1/2. Beta-arrestin binds directly to ERK and may function as a scaffold for the ERK1/2 MAP kinase cascade. ERK directly phosphorylates nuclear transcription factors (ELK) and other substrates (Pearson 2001). These events can all be studied using fragment complementation assays to localize and quantitate the protein-protein complexes and their responses to pathway agonists and antagonists.

To illustrate these examples, we first constructed a cell-based protein-fragment complementation assay to measure the formation of complexes between beta-arrestin2 and the beta-2-adrenergic receptor (see FIGS. 5-6 and 8-10). First, we sought to create a quantitative fluorescence assay for which changes in beta2AR activation would be detected by an increase or decrease in the reconstituted fluorescent signal generated by binding of the receptor to beta-arrestin 2.

Fusion constructs for beta$_2$AR and beta-arrestin2 were prepared as described for Example 1, generating the following constructs: beta2AR-YFP[2] and YFP1-beta-arrestin2. YFP1-beta-arrestin and beta2AR-YFP2 constructs were transfected into HEK293E cells. Following 48 hrs of expression, cells were washed once with Hank's Balanced Salt Solution (HBSS) and treated with 0 to 10 μM of isoproterenol (Sigma-Aldrich Corp., St. Louis, Mo.) for 30 minutes. Treatments were terminated by washing once in HBSS and sequentially fixing and staining the cells with 2% formaldehyde and 3 μg/ml Hoechst dye, respectively, for 15 minutes each. Cells were then washed with HBSS and fluorescence was quantified on a Gemini fluorescence plate reader (Molecular Devices). The mean fluorescence value from untreated cells was subtracted as background from the treatment values. FIG. 5 shows the dose-response for the association of the beta2AR with beta-arrestin2, demonstrating a dose-dependent increase in fluorescence intensity in response to the known receptor agonist (isoproterenol).

To generate a high-content kinetic assay for the association of the beta2AR with beta-arrestin2, a fusion construct for beta-arrestin2 was generated using a mutated version of YFP [1] (SEQ ID No.1) which we designated as IFP[1] (SEQ ID No.5), generating the construct beta-arrestin2-IFP[1]. IFP[1] (SEQ ID No.5) incorporates the mutations F46L, F64L and M153T which have been shown to increase the signal intensity of YFP (Nagai et al. (2002) A variant of yellow fluorescent protein with fast and efficient maturation for cell-biological applications. Nature Biotechnology 20: 87-90). The resulting novel fragment IFP[1] (SEQ ID No.5) is shown below. The mutations in IFP[1] (SEQ ID No.5) relative to YFP[1] (SEQ ID No.5) are capitalized and underlined for emphasis.

```
>IFP1 (SEQ ID No.5)
atggtgagcaagggcgaggagctgttcaccggggtggtgcccatcctggtcgagctggacggcgacgtaaacggcca caagttcagcgtgtccggcgagggcgagggcgatgccacctacggcaagctgaccctgaagttGatctgcaccaccg gcaagctgcccgtgccctggcccaccctcgtgaccaccCtcggctacggcctgcagtgcttcgcccgctacccgac cacatgaagcagcacgacttcttcaagtccgccatgcccgaaggctacgtccaggagcgcaccatcttcttcaagga cgacggcaactacaagacccgcgccgaggtgaagttcgagggcgacaccctggtgaaccgcatcgagctgaagggca tcgacttcaaggaggacggcaacatcctggggcacaagctggagtacaactacaacagccacaacgtctatatcaCg gccgacaagcagtaa >IFP1 (SEQ ID No.6) translation
MVSKGEELFTGVVPILVELDGDVNGHKFSVSGEGEGDATYGKLTLKLICT

TGKLPVPWPTLVTTLGYGLQCFARYPDHMKQHDFFKSAMPEGYVQERTIF

FKDDGNYKTRAEVKFEGDTLVNRIELKGIDFKEDGNILGHKLEYNYNSHN

VYITADKQ
```

The above sequences are the subject of U.S. patent application Ser. No. 10/724,178 filed Dec. 1, 2004 (published as U.S. 2004/0137528 on Jul. 15, 2004) and U.S. patent application Ser. No. 10/772,021 filed Feb. 5, 2004 (published as 2004/0161787 on Aug. 19, 2004). The above two applications are owned by the same assignee of the present application and electronic format sequences were submitted with the above-identified applications.

The constructs beta-arrestin2-IFP[1] and beta2AR-YFP[2] were co-transfected into cells following the methods described for Example 1. After 48 hours cells were treated at 37° C. with 1 micromolar isoproterenol for 1-30 minutes. Cells were fixed and stained as described for FIG. 5. Images of the reconstituted fluorescent signal were acquired on a Discovery-1 instrument (Universal Imaging, Downingtown Pa.) using a 20× objective. FIG. 6 demonstrates a time-dependent change in signal intensity and location in response to agonist as the signal progresses from membrane to intracellular granules. The appearance of the protein-protein complex in intracellular granules is consistent with the process of receptor internalization in response to agonist. FIG. 8 shows the effects of agonist (isoproterenol) and antagonist (propanolol) on the PCA signal at 30', further demonstrating that these high-content assays are dynamically responsive to receptor activation and inhibition and that the known antagonist, propanolol, blocks the effects of isoproterenol. FIG. 9 shows quantitative results for the high-content assay and demonstrates that known agonists increase the amount of the protein-protein complex and that propanolol almost completely blocks the formation of the complex. These assays will be useful in high-content screening to identify novel agonists and antagonists of the beta-adrenergic receptor. Moreover, the assay principle can also be used to construct assays for any GPCR that couples to beta-arrestin, in a manner similar to that shown for the beta-adrenergic receptor, by simply constructing the assay with a cDNA encoding any GPCR of interest fused to a fragment of a suitable reporter, together with a beta-arrestin fused to a complementary fragment of the reporter; and establishing transfection conditions that allow the detection of a robust and reproducible signal. This latter step primarily involves establishing the amount of DNA to be used in the transient transfection, that gives a robust assay signal over background while avoiding massive overexpression of the fusion constructs. Alternatively, stable cell lines can be generated, using for example the methods described below.

EXAMPLE 4

Establishment of Stable Cell Lines and their Use in Drug Screening

For the betaARR2/beta2AR, stable cell lines were generated. HEK293T cells were transfected with the YFP[1]-betaARR2 fusion vector and stable cell lines were selected using 1000 µg/ml Zeocin. Selected cell lines were subsequently transfected with the beta2AR-YFP[2] fusion vector and stable cell lines expressing YFP[1]-betaARR2/beta2AR-YFP[2] were isolated following double antibiotic selection with 200 µg/ml Hygromycin B and 500 µg/ml Zeocin. The fluorescence signals were stable over at least 25 passages (data not shown). Approximately 24 hours prior to drug treatments, cells were seeded into 96 well ploy-D-Lysine coated plates (Greiner) using a Multidrop 384 peristaltic pump system (Thermo Electron Corp., Waltham, Mass). The assay was screened in duplicate against a panel of 98 drugs (names, sources and doses are listed in the table below.

TABLE 3

Drugs and concentrations used in proof-of-principle screening assays

| DRUG | Source | Concentration | DRUG | Source | Concentration | DRUG | Source | Concentration |
|---|---|---|---|---|---|---|---|---|
| (S)-(+)-Camptothecin | Sigma | 500 nM | GGTI-2133 | Calbiochem | 5 microM | Quetiapine | Sequoia | 2 microM |
| 17-AAG | Tocris | 5 microM | Gleevec | Novartis | 10 microM | Raloxifene | LKT Labs, Inc. | 500 nM |

TABLE 3-continued

Drugs and concentrations used in proof-of-principle screening assays

| DRUG | Source | Concentration | DRUG | Source | Concentration | DRUG | Source | Concentration |
|---|---|---|---|---|---|---|---|---|
| Acetyl ceramide | Sigma | 10 microM | Gö 6976 | Calbiochem | 100 nM | Rapamycin | Calbiochem | 250 nM |
| ALLN | Calbiochem | 25 microM | GSK-3 Inh. II | Calbiochem | 1 microM | Risperidone | Sequoia | 2 microM |
| Aminoglutethimide | Microsource | 30 microM | GW1929 | Alexis | 3 microM | Rofecoxib | Sequoia | 10 microM |
| Angiogenin | Sigma | 100 ng/ml | H-89 | Calbiochem | 2 microM | Rolipram | Calbiochem | 25 microM |
| Angiotensin II | Calbiochem | 300 nM | HA14-1 | Tocris | 2 microM | Roscovitine | Calbiochem | 5 microM |
| Apigenin | Calbiochem | 50 microM | Indirubin-3'-Monoxime | Calbiochem | 10 microM | Rosiglitazone | LKT Labs, Inc. | 15 microM |
| Arsenic (III) Oxide | Sigma | 5 microM | Isoproterenol | Sigma | 2 microM | Rosuvastatin | Sequoia | 30 microM |
| ATRA | Sigma | 5 microM | Ketoconazole | Sigma | 30 microM | Rotenone | Sigma | 300 nM |
| BAY 11-7082 | Calbiochem | 10 microM | L-744,832 | Sigma | 10 microM | Salbutamol | Sigma | 2 microM |
| Bicalutamide | Sequoia | 500 nM | Leptomycin B | Sigma | 10 ng/ml | Sarafotoxin S6b | Calbiochem | 100 nM |
| Brefeldin A | Sigma | 50 mg/ml | Letrozole | Sequoia | 1.50 microM | SB 203580 | Calbiochem | 25 microM |
| Caffeine | Sigma | 50 microM | Lithium Chloride | Sigma | 1000 microM | SC-560 | Calbiochem | 250 nM |
| Calyculin A | Calbiochem | 2 nM | Lovastatin | Calbiochem | 30 microM | Sildenafil | Sequoia | 1 microM |
| Celecoxib | Sequoia | 10 microM | LPA | Sigma | 5 microM | Simvastatin | Calbiochem | 30 microM |
| Cerivistatin | Sequoia | 30 microM | LY 294002 | Calbiochem | 25 microM | Tadalafil | Sequoia | 1 microM |
| Ciglitazone | Calbiochem | 15 microM | Mevastatin | Calbiochem | 30 microM | Tamoxifen | Calbiochem | 500 nM |
| Cilostazol | Sigma | 2 microM | MG 132 | Tocris | 1 microM | Taxol | Calbiochem | 2.5 microM |
| Ciprofibrate | Sigma | 30 microM | Milrinone | Sigma | 200 nM | Thalidomide | Calbiochem | 250 microM |
| Clenbuterol | Sigma | 2 microM | MS-275 | Calbiochem | 10 microM | Toremifene | Sequoia | 500 nM |
| Clofibrate | Sigma | 30 microM | Olanzapine | Sequoia | 2 microM | TRAIL | Sigma | 50 ng/ml |
| Clozapine | Sequoia | 2 microM | Paroxetine | Sequoia | 10 microM | Trichostatin A | Calbiochem | 5 microM |
| DBH | Calbiochem | 5 microM | Patulin | Sigma | 10 microM | Troglitazone | Calbiochem | 15 microM |
| Dexamethasone | Sigma | 500 nM | PD 158780 | Calbiochem | 1 microM | Tyrphostin AG 1296 | Calbiochem | 5 microM |
| Epothilone A | Calbiochem | 100 nM | PD 98059 | Calbiochem | 20 microM | Tyrphostin AG 1433 | Calbiochem | 25 microM |
| Estrogen | Calbiochem | 500 nM | PD153035 | Calbiochem | 200 nM | Valdecoxib | Sigma | 10 microM |
| Exemestane | Sequoia | 1.50 microM | Pertussis Toxin | Sigma | 100 ng/ml | Vardenafil | Sequoia | 1 microM |
| Fluvastatin | Calbiochem | 30 microM | Pifithrin-a | Calbiochem | 50 microM | Wortmannin | Calbiochem | 500 nM |
| Fulvestrant | Tocris | 500 nM | Pioglitazone | Calbiochem | 15 microM | Y-27632 | Calbiochem | 25 microM |
| Geldanamycin | Calbiochem | 2.5 microM | Pravastatin | Calbiochem | 30 microM | Ziprasidone | Sequoia | 2 microM |
| Gemfibrozil | Sigma | 30 microM | Propanolol | Calbiochem | 2 microM | ZM 336372 | Calbiochem | 5 microM |
| Genistein | Calbiochem | 12.5 microM | PTPBS | Calbiochem | 500 nM | | | |

Drug concentrations initially were chosen based on literature references and were further refined to ensure lack of toxicity in HEK293 cells, based on lactate dehydrogenase (LDH) toxicity analyses. All liquid handling steps were performed using the Biomek FX platform (Beckman Instruments, Fullerton, Calif.). Cells expressing the betaARR2/beta2AR PCA were incubated in cell culture medium containing drugs for 30 min., 90 min., and 8 hours. Following drug treatments cells were simultaneously stained with 33 micrograms/ml Hoechst 33342 (Molecular Probes) and 15 micrograms/ml TexasRed-conjugated Wheat Germ Agglutinin (WGA; Molecular Probes), and fixed with 2% formaldehyde (Ted Pella) for 10 minutes. Cells were subsequently rinsed with HBSS (Invitrogen) and maintained in the same buffer during image acquisition. YFP, Hoechst, and Texas Red fluorescence signals were acquired using the Discovery-1 automated fluorescence imager (Molecular Devices, Inc.) equipped with a robotic arm (CRS Catalyst Express; Thermo Electron Corp., Waltham, Mass.). The following filter sets were used to obtain images of 4 non-overlapping populations of cells per well: excitation filter 480/40 nm, emission filter 535/50 nm (YFP); excitation filter 360/40 nm, emission filter 465/30 nm (Hoechst); excitation filter 560/50 nm, emission filter 650/40 nm (Texas Red). All treatment conditions were run in duplicate yielding a total of 8 images for each wavelength and treatment condition.

Fluorescence Image Analysis:

For these high-content assays, image analysis is needed to convert the acquired images into fluorescence intensity and, if desired, to resolve the subcellular distribution of the fluorescence signal. A variety of high-content image analysis programs are commercially available; we used the publicly-available program, ImageJ. Raw images in 16-bit grayscale TIFF format were analyzed using ImageJ API/library as described in the literature. First, images from all 3 fluorescence channels (Hoechst, YFP, and Texas Red) were normalized using the ImageJ built-in rolling-ball algorithm [S. R. Sternberg, Biomedical image processing. Computer, 16(1), January 1983]. Next a threshold was established to separate the foreground from background. An iterative algorithm based on Particle Analyzer from ImageJ was applied to the thresholded Hoechst channel image (HI) to obtain the total cell count. The nuclear region of a cell (nuclear mask) was also derived from the thresholded HI. A WGA mask was generated similarly from the thresholded Texas Red image. The positive particle mask was generated from the thresholded YFP image (YI). To calculate the global background (gBG), a histogram was obtained from the un-thresholded YI and the pixel intensity of the lowest intensity peak was identified as gBG. The Hoechst mask, WGA mask and YFP mask were overlapped to define the correlated sub-regions of the cell. The mean pixel intensity for all positive particles within each defined sub-region was calculated, resulting in 4 parameters: total positive pixel mean (MT, the mean intensity of the total particle fluorescence); Hoechst mean (M1, the mean intensity of the Hoechst defined region); Texas Red mean (M2, the mean intensity of the WGA-defined region); and Subtracted mean (M3, the mean intensity of the pixels excluded from the WGA- and Hoechst-defined regions). All means were corrected for the corresponding gBG.

For each set of experiments (assay+drug treatment+treatment time), positive pixel data from eight images were pooled. For each parameter, an outlier filter was applied to filter out those particles falling outside the range (mean±3SD) of the group. Next the sample mean or control mean for each parameter was obtained from each filtered group.

The assay demonstrated a high degree of sensitivity, selectivity and reproducibility. Among the 98 drugs that were tested only a handful of drugs showed an effect which was consistent with known mechanisms of action of those drugs. At early time points the direct agonists such as isoproterenol and salbutamol resulted in an increase in signal intensity. At later times (480 minutes) other agents had effects, including BAY 11-7082; pertussis toxin; and clozapine, which are known to affect GPCR signaling pathways.

EXAMPLE 5

Regulation of GPCR Signaling by the Proteasome: Ubiquitination of Beta-Arrestin

To illustrate another example of a novel assay constructed using the methods provided herein, we developed a protein-fragment complementation assay to measure the association of beta-arrestin2 and ubiquitin (see FIGS. 11-12) using the methods described here. Ubiquitin is a highly conserved 76-amino acid polypeptide. Since its discovery in the mid-1970s, ubiquitin has been associated with cellular housekeeping functions such as eliminating damaged proteins. It has recently become clear that ubiquitin is involved in a variety of other vital processes at different subcellular locations ranging from the plasma membrane to the nucleus, including cell-cycle progression, signal transduction, transcriptional regulation, receptor down-regulation, and endocytosis. Ubiquitin is covalently attached to proteins through an isopeptide bond between its carboxy-terminal glycine and the epsilon-amino group of lysines in the target protein. This attachment is catalyzed by enzymes that activate and ultimately conjugate the ubiquitin moiety to a lysine residue in the substrate. This can be followed by further additions of ubiquitin to specific lysine residues within the linked ubiquitin itself, resulting in a poly-ubiquitin chain. This covalent modification can be reversed by unique proteases specific for the iso-peptide linkage. Although ubiquitin is the best-characterized polypeptide modifier, other polypeptides (often referred to as Ubiquitin-like, or Ubl) are also conjugated to targets in analogous reactions. These 'alternative' modifiers, which differ from ubiquitin in sequence similarity but which are structurally similar to ubiquitin, include SUMO; Nedd8; Hub 1, ISG15 or UCRP; and Apg 12 (reviewed in Aguilar).

Ubiquitinated proteins are recognized by the 19S regulatory subunit of the proteasome, which removes the ubiquitin chain for recycling and denatures the doomed protein. The denatured protein is then fed into the core of the proteasome and reduced to short peptides (less than 22 residues).

A number of proteins that are ubiquitinated have already been identified. These include cyclins and related proteins (cyclins A, B, D, E and cyclin-dependent kinase inhibitors); tumor suppressors, including p53; oncogenes, including c-fos, c-jun, c-myc and N-myc; inhibitory proteins, including IkappaB nad p130; and enzymes, including cdc25 phosphatase, tyrosine aminotransferase, and topoisomerases (I and IIalpha). Copies of two protein motifs—the F-box and the Ring finger, which are believed to identify targets for protein turnover—number in the hundreds in the eukaryotic genome suggesting a large number of proteins whose turnover is regulated by the ubiquitin system.

In addition to the proteasome machinery itself, the regulatory events upstream of the proteasome (that is, phosphorylation and ubiquitination of proteasome substrates and their regulators) are being actively explored for drug discovery. The selectivity of protein degradation is determined mainly at the stage of ligation to ubiquitin. Briefly, ubiquitin-protein ligation requires the sequential action of three enzymes. Ubiquitin must first become attached to a member of the family of E2 ubiquitin-conjugating enzymes (an E1 ubiquitin-activating enzyme provides the initial ATP-dependent activation). Subsequently, the E2 enzyme itself, or, more typically, an E3 ligase, provides the specificity for the transfer of ubiquitin onto the targeted protein (ligase substrate). Usually there is a single E1, but there are many species of E2s and multiple families of E3s or E3 multiprotein complexes. Specific E3s appear to be responsible mainly for the selectivity of ubiquitin-protein ligation (and thus, of protein degradation). They do so by binding specific protein substrates that contain specific recognition signals. In some cases, binding of the substrate protein to an E3 is indirect, via an adaptor protein. The identification of the E3 ubiquitin ligases as proteins containing protein-protein interaction domains that couple to the ubiquitin-charged E2 (ubiquitin-conjugating) enzyme provided the link between substrate recognition and the catalytic steps for ubiquitin chain formation.

Agonist-stimulated ubiquitination of the beta-2-adrenergic receptor, and of beta-arrestin2, has been reported as essential for receptor internalization. Proteasomal inhibitors such as lactacystin and ALLN are cell-permeable compounds that specifically block the activity of the 26S proteasome and cause accumulation of those ubiquitinated proteins that are degraded by proteasomes.

Previously, assays for ubiquitination have relied upon immunoblotting of proteins with anti-ubiquitin antibodies, or on labelling of proteins with a fluorophore-tagged ubiquitin polypeptide. Here we demonstrate the construction of cell-based assays for the direct measurement of ubiquitination by measuring the formation of a complex between ubiquitin and beta-arrestin-2. Assays were constructed using the methods described above for the YFP PCA in which the protein-protein pair used in the transfection was the betaAR2 construct described above (beta-arrestin2-IFP[1]) together with the ubiquitin monomer (Genbank identifier NM_021009-CDS 69 . . . 296) with the F2 fragment of YFP fused at the N-terminus of the Ubiquitin cDNA. FIGS. 11-12 show the results of the transient transfection of the PCA constructs. To demonstrate that the assay was capable of detecting the effects of drugs, we tested the effects of the beta-adrenergic agonist, isoproterenol, and the proteasome inhibitor, ALLN, on the signal intensity. Since the process of ubiquitination targets proteins for degradation, we used ALLN (see Table 3 for concentration) to inhibit the proteasome activity of the cell in order to ensure that the arrestin/ubiquitin complex would accumulate in the cells and be detectable. The assay signal was clearly visible in the presence of ALLN (FIG. 11, upper left panel) even in the absence of isoproterenol. However, treatment of the cells with isoproterenol for 60-120 minutes caused a significant increase in fluorescence intensity (FIG. 11). FIG. 12 shows the effects of the MG132, a proteasome inhibitor, and Trichostatin A, an inhibitor of histone deacetylase (HDAC), on the fluorescence signal as compared with the negative (vehicle-only) control. Both drugs significantly increased the assay signal, as shown. The effects of Trichostatin A are particularly interesting in light of recent findings linking HDAC inhibition with the attenuation of cardiac hypertrophy induced by isoproterenol or by overexpression of proteins linked to cardiac growth and proliferation (Cardiac hypertrophy and histone deacetylase-dependent transcriptional repression mediated by the atypical homeodomain protein Hop; H. Kook, et al., J Clin Invest. 2003 September; 112(6):863-71). These authors discuss the finding that chromatin remodeling and repression of otherwise active transcriptional processes can result in hypertrophy and heart failure, and that this process can be blocked with chemical HDAC inhibitors suggesting a connection between HDAC and GPCR-dependent signaling events. HDAC inhibitors are already in clinical trials for a variety of noncardiac disorders and could potentially influence normal or pathological cardiac function. The identification and further elucidation of antihypertrophic transcriptional pathways will offer novel therapeutic targets for the treatment of congestive heart failure. Our results show an increase in ubiquitin/arrestin complexes in the presence of Trichostatin A and suggest that these assays will be useful in high-throughput screening to further elucidate the pathways leading to cardiac hypertrophy and to identify novel inhibitors of the proteasome and of HDACs; in addition to identifying other ubiquitinated proteins and other components of the proteasome and HDAC regulatory pathways.

EXAMPLE 6

PCA Fragments are not Optically Detectable Molecules

It is important to note the key distinctions between the present invention and previous cell-based assays involving a β-arrestin tagged with GFP. In the latter assays, a single fusion construct comprising a beta-arrestin tagged with an optically detectable molecule, such as an intact GFP, is introduced into a cell. Therefore, what is visualized or quantified is the amount of the expressed beta-arrestin protein.

In contrast, in the present invention, β-arrestin is tagged with an inactive fragment of a reporter. To demonstrate the lack of optical activity of the fragments, HEK293E cells were transfected with equal amounts of either the β-arrestin2-IFP[1] or β2AR-YFP[2] fusion construct DNA, or co-transfected with both beta-arrestin2-IFP[1] and β2AR-YFP[2]. After 48 hours cells were treated at 37° C. with 10 micromolar isoproterenol for 30 minutes. Cells were fixed and stained as described for FIG. 5. Images of the reconstituted fluorescent signal (upper panel) and the Hoechst-stained nuclei (lower panel) were acquired on a Discovery-1 instrument (Universal Imaging, Downingtown Pa.) using a 20× objective.

As shown in FIG. 7, when transfected singly, this beta-arrestin-fragment fusion does not generate a detectable signal (compare to No DNA control). Neither does the complementary fragment, fused to the beta-2-adrenergic receptor, generate a signal. Therefore, the PCA fragment is not an optically detectable molecule.

The same is true for all previously-created PCAs that are referenced in the present specification. PCA requires the co-expression of two molecules that form a complex. When complementary fragments are brought into proximity by the molecules to which they are fused, the fragments are capable of folding and reassembling, or complementing. It is a characteristic of PCA that a signal is generated only upon assisted complementation.

Moreover, the present invention is not equivalent in any aspect to previous inventions in which a single protein is tagged with an optically detectable molecule, such as described by Barak et al. (U.S. Pat. Nos. 5,891,646 and 6,110, 693). These inventions measure completely different phenomena. In the case of tagging a protein such as beta-arrestin with a fluorescent protein or some other optically detectable molecule, what is imaged or quantified in the assay is the amount of an individual, tagged protein and/or the subcellular location of an individual, tagged protein. This is not possible with fragment complementation, since the individual proteins tagged with fragments do not generate an optically detectable signal (FIG. 7). In contrast, what is quantified with PCA as in FIG. 5 is the association of two proteins; and what is imaged with PCA as in FIG. 6 and FIG. 8 is the subcellular location of the protein-protein complex.

EXAMPLE 7

Assays for Other Elements of G-Protein-Coupled Pathways

Table 1 describes a large number of assays that can be created for GPCR pathways. FIG. 13 (A-C) demonstrates fragment complementation assays for some of these elements; transient transfections are shown. We teach that the methods provided here are not limited to any particular GPCR or downstream event. Here we provide examples of fragment complementation assays for a variety of 7TM receptors including the Frizzled homolog 4 (Frizzled4) (FIG. 13A); the Chemokine Receptor 5 (FIG. 13B); the vasoactive intestinal peptide receptor 2 (VIPR2) and the somatostatin receptor (FIG. 13C) along with various 'downstream' elements of GPCR signaling pathways.

Frizzled homolog 4 is a member of the frizzled gene family. Members of this family encode seven-transmembrane domain proteins and current evidence indicates that the Frizzled family of proteins act as receptors for Wnt family ligands. Recent studies have shown that increased activity of the Wnt signaling pathway, mediated by stabilization of β-catenin, is an important aspect of carcinogenesis in human melanomas and colorectal cancers, making this an important pathway for drug discovery. FIG. 13A shows that Frizzled homolog 4 interacts with G-alpha-I, RGS2, and GRK2 in human cells and that robust fluorescence assays can be generated for these protein-protein complexes based on the fragment complementation assays taught herein.

Chemokine Receptor 5 (FIG. 13B): Chemokine receptors were recently shown to play an important role in human immunodeficiency virus type 1 (HIV-1) infection by serving as essential cofactors for HIV-1 entry. Chemokines are 70-90 amino acid major inflammatory peptides that have been implicated in migration and activation of leukocytes. They can be subdivided into CXC and CC subfamilies according to the position of conserved cysteine residues, which are either separated by one amino acid (X) or are adjacent to one another. CXC chemokines predominantly activate neutrophils and appear to be important in acute inflammatory responses, whereas CC chemokines generally target myeloid and lymphoid cells as well as basophils and eosinophils and are thought to be involved in chronic and allergic inflammation. Chemokines bind to a family of G protein-coupled receptors (GPCRs) that are differentially expressed in blood cells. CXC chemokines bind CXC-specific receptor subtypes (CXCR-1, CXCR-2, CXCR-3 and CXCR-4) and CC chemokines recognize a second subgroup of chemokine receptors (CCR-1, CCR-2a, CCR-2b, CCR-3, CCR-4 and CCR-5), each of which shows distinct but overlapping ligand binding specificity. Although identification of CCR-5 as a cofactor for HIV-1 infection represents a breakthrough, little is known about signal transduction and regulation of this chemokine receptor. In general, agonist binding to GPCRs activates a signaling cascade mediated by intracellular second messengers, which is counteracted by intrinsic cellular mechanisms which rapidly attenuate receptor signaling. The process involves phosphorylation by second messenger-dependent protein kinases and receptor-specific G protein-coupled receptor kinases (GRKs), which facilitate binding of arresting proteins (beta-arrestins) to the receptor, resulting in further uncoupling of receptor-G protein interactions. In addition, beta-arrestins participate in receptor sequestration/internalization, the process responsible for re-establishment of normal responsiveness, by serving as GPCR adaptor proteins. GRK-mediated phosphorylation may represent a common mechanism by which chemokine receptor desensitization is achieved. Previous studies have shown that CCR-5 can be phosphorylated by GRK2, -3, -5 and -6. We show a direct interaction between the chemokine receptor and GRK. Beta-arrestin/CCR assays can also be constructed, in addition to assays for a number of known or novel proteins downstream of CCRs in the signaling cascade (e.g. Table 2). FIG. 13B shows that CCR5 interacts with PKCalpha generating a bright fluorescence assay. The assays we teach in the present invention will be useful in identifying the signaling pathways controlled by chemokine receptors and in screening drug candidates that act on these pathways.

Vasoactive intestinal peptide receptor 2 (VIPR2): Vasoactive intestinal peptide (VIP) is a 28 amino acid peptide (human, chr 6q26-q27). It is expressed and secreted by neurons innervating primary and secondary immune organs such as lymph nodes with a molecular weight of 20 kD. VIP is a potent neurotrophic factor causes vasodilation, lowers arterial blood pressure, and relaxes the smooth muscle of trachea, stomach and gall bladder. VIP also modulates several T-lymphocyte activities including motility, cytokine production, proliferation and apoptosis. VIPR2, a 438aa (chr.7q36.3) protein in human (437aa in rat and mouse). The VIP receptor2 (VIPR2) is also termed as type III PACAP receptor, mainly expressed in neural tissues. This is a receptor for VIP as well as PACAP 38 and 27. The activity of VIPR2 is mediated by G proteins, which activate adenyl cyclase and can be coupled to phospholipase C. FIG. 13C shows that VIPR2 interacts with the G-protein, G-beta-1, generating a robust fluorescence assay. The assays we teach in the present invention will be useful in identifying the signaling pathways controlled by VIPR2 and in identifying novel drug candidates that act on these pathways.

Somatostatin receptor Type 2 (FIG. 13C): SSTR2 is the receptor for somatostatins-14 and -28. This receptor is coupled via pertussis toxin sensitive G proteins to inhibition of adenylyl cyclase. Somatostatin is growth-inhibitory for certain tumor cells. Somatostatin is a widely expressed hormone that exerts pleiotropic biological actions, including neurotransmission, inhibition of hormonal and hydroelectrolytic secretions, and cell proliferation. This neuropeptide acts by interacting with specific receptors that belong to the G protein-coupled seven-transmembrane domain receptor (GPCR) superfamily. Five subtypes of somatostatin receptors have been thus far cloned (SSTR1-5). They mediate a variety of signal transduction pathways, including inhibition of adenylate cyclase and guanylate cyclase, modulation of ionic conductance channels and protein phosphorylation, activation of mitogen-activating protein kinase and phospholipase C. Among somatostatin receptors, sst2 has been found to play a critical role in the negative control of cell growth and to act as a tumor suppressor gene for pancreatic cancer. The signaling pathways, for SSTR2 receptor-mediated cell growth inhibition have not been fully elucidated. FIG. 13C shows that SSTR2 interacts with G-beta-1, generating a robust fluorescence assay. The assays we teach in the present invention will be useful in identifying the signaling pathways controlled by SSTR2 and in identifying novel drug candidates that act on these pathways.

Details of Various GPCR Signaling Proteins

1) RGS Proteins (Regulators of G-protein Signaling)

A large superfamily of GTPase-accelerating proteins that numbers over 30 members has been identified and named "RGS" (Regulators of G-protein Signaling) (R J Kimple et al., 2003, Established and emerging fluorescence-based assays for G-protein function: heterotrimeric G-protein alpha subunits and RGS proteins, Combinatorial Chem. & HTS 6: 1-9). Each RGS protein contains a hallmark domain, or RGS-box which contacts the Ga switch regions. Many RGS proteins have been shown to catalyze rapid GTP hydrolysis by isolated G$\alpha$ subunits and to attenuate agonist/GPCR-stimulated cellular responses in vivo. RGS proteins may play various roles, functioning as key desensitizers of GPCR pathways; as heterotrimeric G-protein effectors; effector antagonists; and/or scaffolds that regulate the kinetics and specificity of GPCR signal transduction. Moreover, RGS proteins represent some of the best drug discovery targets in GPCR pathways. They are a highly diverse protein family, have unique tissue distributions, are strongly regulated by signal transduction events, and will likely play diverse functional roles in living cells. Drugs targeting RGS proteins can be divided into five groups: 1) potentiators of endogenous agonist function, 2) potentiators/desensitization blockers of exogenous GPCR agonists, 3) specificity enhancers of exogenous agonists, 4) antagonists of effector signaling by an RGS protein, and 5) RGS agonists.

Previously, interactions between G-alpha subunits and RGS proteins were measured by biochemical methods including affinity chromatography or surface plasmon resonance. More recently, FRET has been used to study the G$\alpha$/RGS interactions. For example, interactions between RGS and G$\alpha$ have been studied by fusing CFP to G$\alpha$i1 and fusing YFP to RGS4 and measuring FRET. The present invention encompasses PCAs for the measurement of RGS interactions with G-proteins and other elements of GPCR pathways. As for other PCAs, either high-throughput or high-content assays can be constructed, enabling studies of the induction or inhibition of protein-protein complexes as well as their trafficking between subcellular compartments.

FIG. 13A (middle panel) demonstrates a novel assay for RGS2 in association with the Frizzled homolog 4 protein. These assays should be useful not only in drug discovery but in understanding the biological mechanisms underlying wnt/frizzled signaling. The known elements of the Frizzled signaling pathway are poorly understood including the mechanisms by which signals from the ligand (Wnt) and receptor (Frizzled) to downstream components such as Axin, glycogen synthase kinase 3 (GSK3), adenomatous polyposis coli protein (APC), and β-catenin are transmitted. APC, the gene for adenomatous polyposis coli, is a known tumor suppressor, and β-catenin is an oncogene. Axin, in complex with APC and GSK3, negatively regulates the transcription factor β-catenin, in part by causing its ubiquitination and degradation. Wnt binding to its receptor, Frizzled, relieves this inhibitory effect thus increasing levels of active β-catenin. The recent crystal structure of an Axin/APC complex revealed that APC binds to the RGS domain of Axin. The assay we present here may be useful in discovering drug candidates capable of blocking or activating the wnt/frizzled pathway and in elucidating the components of the pathway important for a variety of disorders in man.

2) RAMPS (Receptor-Activity-Modifying Proteins)

A family of accessory single-transmembrane proteins, RAMPS (receptor-activity-modifying proteins) has been identified and found to complex with the calcitonin-receptor-like receptor (CRLR). The association of CRLR with RAMPs plays a role not only in targeting the receptor to the cell surface, but also in modifying the pharmacological properties of the receptor. Various homologues of RAMP proteins have been identified. While RAMP1 converted CRLR into a calcitonin-gene-related peptide (CGRP) receptor, RAMP2-associated receptors display the properties of an adrenomedullin receptor (Gether 282). PCAs for the detection and quantitation of complexes between GPCRs and RAMPs can readily be constructed using the principles and methods described herein, which will enable a thorough functional characterization of these mechanisms and their responses to biological agents and novel compounds.

3) Phospholipase C

Stimulation of phosphoinositide-hydrolyzing phospholipase C (PLC) is a cellular response to activation of a wide variety of membrane receptors, including numerous GPCRs as well as several receptor tyrosine kinases (RTKs). These two types of membrane receptors generally stimulate distinct PLC isoenzymes. GPCRs activate PLCβ isoenzymes, either via GTP-liganded alpha-subunits of the Gq class of G proteins or by beta-gamma dimers liberated from Gi-type G proteins. In contrast, RTKs, such as those for EGF and PDGF receptors, activate PLCγ isoenzymes by recruitment of these PLCs to the autophosphorylated RTKs and subsequent tyrosine phosphorylation.

4) Protein Kinases and Protein Phosphatases

A variety of protein kinases are integral to G-protein-coupled receptor regulation and pathway activity. First, GPCRs are phosphorylated by G-protein-coupled receptor kinases (GRKs). GRKs are serine/threonine kinases that preferentially phosphorylate receptors that are occupied by agonists. FIG. 13A shows a novel assay for the association of GRK2 with Frizzled 4.

GRKs participate in homologous receptor desensitization and the subsequent binding of beta-arrestin. There are seven known GRKs. Rhodopsin kinase (GRK1) and GRK7, a candidate for a conde opsin kinase, are retinal kinases involved in the regulation of thodopsin photoreceptors, whereas GRK2-GRK6 are more widely expressed. Membrane targeting of all the GRKs is apparently critical to their function and is conferred by a C-terminal tail domain. GRK1 and GRK7 each possess a C-terminal CAAX motif. Light-induced translocation of GRK1 from the cytosol to the membrane is facilitated by the post-translational farnesylation of this site. The beta-adrenergic receptor kinases (GRK2 and GRK3) have C-terminal G-beta-gamma subunit binding and pleckstrin-homology domains, and they translocate to the membrane as a result of interactions between these domains and free G-beta-gamma subunits and inositol phospholipids. Palmitoylation of GRK4 and GRK6 on C-terminal cysteine residues leads to constitutive membrane localization. Targeting of GRK5 to the membrane is thought to involve the interaction of a 46-resude C-terminal domain with membrane phospholipids.

Assays for GRK interactions with their cognate proteins and substrates are a subject of the present invention. GRK interactions with GPCRs, with G-protein subunits, with beta-arrestin, with farnesyl transferase or other lipid transferases, and with a variety of downstream kinases and other signaling proteins can all be investigated using fragment complementation assays. Due to the post-translational modifications of the C-terminus of GRK and its role in proper subcellular localization, reporter fragments should be fused at the amino terminus of GRK.

The Ras-dependent activation of the ERK1/2 MAP kinase pathway by many GPCRs requires activity of the tyrosine kinase, c-Src. In some cases, the known interaction between β-arrestin and Src appears to be important for GPCR-mediated ERK1/2 activation. In HEK-293 cells, overexpression of beta-arrestin1 mutants that exhibit either impaired Src binding or are unable to target receptors to clathrin-coated pits blocks beta-2-adrenergic receptor-mediated activation of ERK1/2. In KNRK cells, activation of NK1 receptor by substance P leads to assembly of a scaffolding complex containing the internalized receptor, β-arrestin, Src and ERK1/2. Expression of either a dominant-negative β-arrestin 1 mutant or a truncated NK1 receptor that fails to bind to β-arrestin blocks complex formation and inhibits both substance-P-stimulated endocytosis of the receptor and activation of ERK1/2.

Taken together these results suggest that it might be possible to demonstrate direct interactions between the kinases GRK, PKC and Src. FIG. 13B demonstrates that this is indeed the case. We show novel assays for GRK association with protein kinase C (PKCalpha) and with the c-Src kinase. In addition FIG. 13C demonstrates a novel assay for GRK association with transcription factor ERK2.

Small-molecule inhibitors of GRKs have not yet been reported. Assays for GRK could be used in high-throughput or high-content screening to identify inhibitors of GRKs. Such inhibitors would be expected to produce prolonged activation of their cognate GPCRs.

5) Protein Phosphatases

Shortly after stimulation, phosphorylated beta-2 adrenergic receptors appear in an endosomal vesicle fraction that is enriched in GPCR-specific protein phosphatase 2A (Pitcher et al 1995) which dephosphorylates the receptor. The association and dissociation of PPP2A and other phosphatases with GPCRs can be measured using fragment complementation assays.

6) Other G-Protein-Coupled Pathway Elements Suitable for Fragment Complementation Assays A large number of other G-protein-coupled pathway elements are suitable for use under the present invention. This includes those proteins listed in Table 2 and in the references provided throughout this application, and any homologues thereof. The invention can be applied to any 7-transmembrane receptor from any species, including but not limited to those found in human GPCR databases. The present invention can be applied to novel or orphan GPCRs and novel elements of G-protein-coupled pathways that may be identified by the methods provided herein or by other methods for mapping pathways and identifying protein-protein interactions. Such alternative methods are well known by those skilled in the art and may include yeast two-hybrid approaches, phage display, and mass spectroscopy for the analysis of protein-protein complexes.

The entire contents including the references cited therein of the following patents including all their foreign equivalents and publications are incorporated by reference in their entirety for all purposes to the same extent as if each individual patent, patent application or publication were so individually denoted.

U.S. Patent Documents

U.S. Pat. No. 6,270,964 Michnick, et al.
U.S. Pat. No. 6,294,330 Michnick, et al.
U.S. Pat. No. 6,428,951 Michnick, et al.
U.S. Patent Application 20030108869 Michnick, et al.
U.S. Patent Application 20020064769 Michnick, et al.
U.S. Pat. No. 6,342,345 Blau, et al.
U.S. Pat. No. 5,891,646 Barak, et al.
U.S. Pat. No. 6,110,693 Barak, et al.
U.S. Pat. No. 6,255,059 Klein, et al.
U.S. Patent Application 20020022238 King et al.

OTHER PUBLICATIONS

L S Barak, S S Ferguson, J Zhang and M G Caron, 2001, A beta-arrestin/green fluorescent protein biosensor for detecting G-protein-coupled receptor activation. J. Biol. Chem. 272: 27497-27500.

J N Pelletier, I Remy, I. and S W Michnick, 1998, Protein-Fragment Complementation Assays: a General Strategy for the in vivo Detection of Protein-Protein Interactions. Journal of Biomolecular Techniques 10: 32-39.

I Remy, J N Pelletier, A Galarneau & S W Michnick, 2002, Protein Interactions and Library Screening with Protein Fragment Complementation Strategies. in: Protein-protein interactions: A molecular cloning manual. E. A. Golemis, editor. Cold Spring Harbor Laboratory Press. Chapter 25, 449-475.

S W Michnick, I Remy, F X C-Valois, F. X., A Vallee-Belisle, A. Galarneau & J N Pelletier, 2000, Detection of Protein-Protein Interactions by Protein Fragment Complementation Strategies, Parts A and B (John N. Abelson, Scott D Emr and Jeremy Thomer, editors) Methods in Enzymology 328: 208-230.

I Remy, I A Wilson & S W Michnick, 1999, Erythropoietin receptor activation by a ligand-induced conformation change. Science 283: 990-993.

I Remy & S W Michnick, 2001, Visualization of Biochemical Networks in Living Cells. Proc Natl Acad Sci USA 98: 7678-7683.

Rossi, 1997, Monitoring protein-protein interactions in intact eukaryotic cells by beta-galactosidase complementation. Proc Natl Acad Sci USA 94: 8405-8410, 1997.

J M Spotts, R E Dolmetsch, & M E Greenberg, 2002, Time-lapse imaging of a dynamic phosphorylation-dependent protein-protein interaction in mammalian cells, Proc. Natl. Acad. Sci. USA 99: 15142-15147.

Although the present invention has been described with reference to specific details of certain embodiments thereof, it is not intended that such detail should be regarded as limitations upon the scope of the invention, except as and to the extent that they are included in the accompanying claims.

What is claimed is:

1. A method of screening a candidate drug, a compound library or a biological extract to identify activators or inhibitors of G-protein-coupled receptors or G-protein-coupled pathways using fluorescent protein complementation assays, said method comprising the steps of:
   (A) selecting a fluorescent protein reporter molecule;
   (B) effecting fragmentation of said fluorescent protein reporter molecule such that said fragmentation results in reversible loss of reporter function;
   (C) fusing or attaching fragments of said fluorescent protein reporter molecule separately to interacting protein molecules associated with G-protein-coupled receptors or G-protein- coupled pathways;
   (D) transfecting cells with nucleic acid constructs coding for the products of step (C);
   (E) testing the effects of said candidate drug, compound library, or biological extract on the receptor or pathway of interest by contacting said cells as defined in step (D) with said candidate drug, compound library or biological extract; and
   (F) measuring and/or detecting the fluorescence resulting from the reassociation of the reporter fragments which had been fused to the interacting proteins, to identify specific agents that activate or inhibit the receptor or pathway of interest.

2. A method for identifying a drug lead that modulates the activity of a G-protein-coupled pathway using fluorescent protein complementation assays, said method comprising the steps of:
   (a) assembling a collection or a library of compounds, said collection or library selected from the group consisting of candidate drugs, natural products, chemical compounds and/or biological extracts;
   (b) selecting a fluorescent protein reporter molecule;
   (c) effecting fragmentation of said fluorescent protein reporter molecule such that said fragmentation results in reversible loss of reporter function;

(d) fusing or attaching fragments of said fluorescent protein reporter molecule separately to said interacting protein molecules associated with a G-protein-coupled pathway;
(e) transfecting cells with nucleic acid constructs coding for the products of step (d);
(f) screening said collection or library by contacting said cells as defined in (e) with one or more test elements from said collection or library; and
(g) detecting by the fluorescence resulting from the reassociation of the reporter fragments which had been fused to the interacting proteins, one or more properties of said assay; wherein a change in one or more properties of said assay in the presence of any of said test elements, relative to the absence of said test element, is used to identify a drug lead that modulates a G-protein-coupled pathway.

3. A method according to claims 1 or 2 wherein the method is used to identify agonists, antagonists, activators or inhibitors of G-protein coupled receptors or G-protein-coupled pathways.

4. A method according to claims 1 or 2 wherein said method is performed to screen for compounds from a biological extract or from a synthetic, combinatorial, natural product, peptide, antibody, or nucleic acid library that activate or inhibit a G-protein-coupled receptor or a G-protein-coupled pathway.

5. A method according to claims 1 or 2 wherein said method is performed to identify a ligand for a G-protein coupled receptor.

6. A method or assay according to claims 1 or 2 comprising at least one molecule fused to a reporter fragment, wherein said molecule is selected from the group consisting of: a 7-transmembrane receptor, a ligand, an alpha subunit of a guanine nucleotide binding protein, a beta subunit of a guanine nucleotide binding protein, a gamma subunit of a guanine nucleotide binding protein, a phosphodiesterase, an arrestin molecule, a receptor-activity-modifying protein (RAMP), an adenylate cyclase, an A-kinase anchoring protein (AKAP), an RDG molecule, an RGS molecule, a phospholipase, a protein kinase, a protein phosphatase, a cytokine receptor, a growth factor receptor, a cytoskeletal protein, an E3 ligase, a ubiquitin molecule, a SUMO molecule, a G-protein-coupled inwardly rectifying K+ channel (GIRK), a Na+/H+ exchanger regulatory factor, a PDZ-containing protein, a Homer-domain protein, an EVH-containing protein, a Dishevelled-like protein, a farnesyl transferase, a palmitoyl transferase, a myristoyl transferase, a ribosomal protein P2, an N-ethylmaleimide-sensitive fusion protein (NSF), a clathrin, and a transcription factor.

7. A method of assaying protein-protein interactions associated with a G-protein-coupled receptor or a G-protein-coupled pathway using fluorescent protein complementation assays, said method comprising the steps of:
(a) identifying protein molecules that interact, wherein said protein molecules are selected from the group consisting of: a 7-transmembrane receptor, a ligand for a G-protein coupled receptor, an alpha subunit of a guanine nucleotide binding protein, a beta subunit of a guanine nucleotide binding protein, a gamma subunit of a guanine nucleotide binding protein, a phosphodiesterase, an arrestin molecule, a receptor-activity-modifying protein (RAMP), an adenylate cyclase, an A-kinase anchoring protein (AKAP), an RDG molecule, an RGS molecule, a phospholipase, a protein kinase, a protein phosphatase, a cytokine receptor, a growth factor receptor, a cytoskeletal protein, an E3 ligase, a ubiquitin molecule, a SUMO molecule, a G-protein-coupled inwardly rectifying K+ channel (GIRK), a Na+/H+ exchanger regulatory factor, a PDZ-containing protein, a Homer-domain protein, an EVH-containing protein, a Dishevelled-like protein, a farnesyl transferase, a palmitoyl transferase, a myristoyl transferase, a ribosomal protein P2, an N-ethylmaleimide-sensitive fusion protein (NSF), a clathrin, and a transcription factor;
(b) selecting a fluorescent protein reporter molecule;
(c) effecting fragmentation of said fluorescent protein reporter molecule such that said fragmentation results in reversible loss of reporter function;
(d) fusing or attaching fragments of said fluorescent protein reporter molecule separately to said interacting protein molecules as defined in step (a);
(e) transfecting cells with nucleic acid constructs coding for the products of step (d);
(f) reassociating said reporter fragments through interactions of the protein molecules that are fused or attached to said fragments; and
(g) measuring the fluorescent activity of said reporter molecule resulting from the reassociation of said reporter fragments.

8. A method according to claims 7, 1 or 2 whereby the molecules fused to the fluorescent protein reporter fragments are identified by a method chosen from the group consisting of: (a) cDNA library screening; (b) pairwise interaction mapping; and (c) prior knowledge of the existence of an interaction between a of proteins.

* * * * *